(12) United States Patent
Richardson et al.

(10) Patent No.: US 7,316,738 B2
(45) Date of Patent: Jan. 8, 2008

(54) MILLED SUBMICRON CHLOROTHALONIL WITH NARROW PARTICLE SIZE DISTRIBUTION, AND USES THEREOF

(75) Inventors: Hugh W. Richardson, Sumter, SC (US); Robert L. Hodge, Sumter, SC (US)

(73) Assignee: Phibro-Tech, Inc., Ridgefield Park, NJ (US)

( * ) Notice: Subject to any disclaimer, the term of this patent is extended or adjusted under 35 U.S.C. 154(b) by 0 days.

(21) Appl. No.: 10/961,155

(22) Filed: Oct. 12, 2004

(65) Prior Publication Data

US 2006/0075921 A1    Apr. 13, 2006

Related U.S. Application Data

(60) Provisional application No. 60/616,646, filed on Oct. 8, 2004.

(51) Int. Cl.
*A01N 37/34* (2006.01)
*A01N 33/00* (2006.01)
*C09D 5/14* (2006.01)

(52) U.S. Cl. ............... 106/18.32; 106/18.35; 424/405; 514/741; 558/411; 558/425; 570/182

(58) Field of Classification Search .......... 106/18.32, 106/18.35; 514/360, 741; 424/405; 558/411, 558/425; 570/182
See application file for complete search history.

(56) References Cited

U.S. PATENT DOCUMENTS

| | | | |
|---|---|---|---|
| 4,075,326 | A | 2/1978 | Kuyama et al. |
| 4,923,894 | A | 5/1990 | Kanda et al. |
| 5,145,684 | A | 9/1992 | Liversidge et al. |
| 5,277,979 | A | 1/1994 | Kielbania, Jr. et al. |
| 5,304,376 | A | 4/1994 | Friedrichs et al. |
| 5,360,783 | A | 11/1994 | Itoh et al. |
| 5,536,305 | A | 7/1996 | Yu |
| 5,552,378 | A | 9/1996 | Trinh et al. |
| 5,667,795 | A | 9/1997 | Fraley |
| 5,714,507 | A | 2/1998 | Valcke et al. |
| 5,874,025 | A | 2/1999 | Heuer et al. |
| 5,874,476 | A | 2/1999 | Hsu et al. |
| 6,074,986 | A | 6/2000 | Mulqueen et al. |
| 6,521,288 | B2* | 2/2003 | Laks et al. .......... 427/180 |
| 6,753,035 | B2 | 6/2004 | Laks et al. |
| 2001/0051175 | A1 | 12/2001 | Strom et al. |
| 2002/0047058 | A1 | 4/2002 | Verhoff et al. |
| 2002/0051892 | A1 | 5/2002 | Laks et al. |
| 2002/0055046 | A1 | 5/2002 | Ono et al. |
| 2003/0040569 | A1 | 2/2003 | Curry et al. |
| 2003/0127023 | A1 | 7/2003 | Grandidier et al. |
| 2004/0024099 | A1 | 2/2004 | Narayanan |
| 2004/0050298 | A1 | 3/2004 | Giger et al. |
| 2004/0063847 | A1 | 4/2004 | Curry et al. |
| 2004/0176477 | A1 | 9/2004 | Davison et al. |
| 2004/0258767 | A1* | 12/2004 | Leach et al. .......... 424/630 |
| 2004/0258768 | A1 | 12/2004 | Richardson et al. |
| 2005/0118280 | A1* | 6/2005 | Leach et al. .......... 424/617 |

FOREIGN PATENT DOCUMENTS

| | | |
|---|---|---|
| EP | 0472973 A1 | 3/1992 |
| WO | 2004/091875 | 10/2004 |
| WO | 2005/007368 | 1/2005 |
| WO | 2005/110692 | 11/2005 |
| WO | 2005/115704 | 12/2005 |

OTHER PUBLICATIONS

"Use of Nanoparticles for Controlled Release of Biocides in Solid Wood" by Liu et al., Journal of Applied Polymer Science, Wiley and Sons pub., pp. 458-465. (2001), no month.
Backman et al. "The effects of particle size and distribution on performance of the fungicide chlorothalonil" Phytopathology 66:1242-1245 (1976) (no month).
Liu et al. "Use of Nanoparticles for the Controlled Release of Biocides in Pressure-Treated Solid Wood" Polymer Preprints 38(2):624-625 (1997) (no month).
Liu et al. "Use of Polymeric Nanoparticles for Controlled Release of Biocides in Solid Wood" Abstract, GG3.4, Symposium GG Polymeric Materials - Drugs, Delivery and Devices Nov. 30 - Dec. 1 (1998), Proceedings published as vol. 550 of the Materials Research Society Symposium Proceedings Series.
Liu, "Use of Polymer Nanoparticles as Carriers for the Controlled Release of Biocides in Solid Wood," Dissertation for the Degree of Ph. D., Michigan Technological University (1999) (no month).
The Copper Champs! Unique Copper hydroxide Formulations (Brochure), Nufarm Americas Inc. (2002)(no month).

* cited by examiner

*Primary Examiner*—Anthony J. Green
(74) *Attorney, Agent, or Firm*—Morgan, Lewis & Bockius LLP

(57) ABSTRACT

A method of milling chlorothalonil to form a sub-micron product having a narrow particle size distribution is presented. The milling involves wet milling of the chlorothalonil with high density milling media having a diameter between 0.1 mm and 0.8 mm, preferably between 0.2 mm and 0.7 mm, and a density equal to or greater than 3.8 g/cc, preferably greater than 5.5 g/cc, in a ball mill using between about 40% and 80% loading of the mill volume with milling media, and having the chlorothalonil suspended in an aqueous milling liquid which comprises one or more surface active agents. The milling speed is preferably high, for example from about 1000 rpm to about 4000 rpm. The milled product can be used in foliar applications at a lower effective dosage than prior art formulations, can be used in improved antifouling paint formulations, and can be used in new applications such as the direct injection of solid chlorothalonil particulates in wood to act as a long lasting wood preservative.

26 Claims, 3 Drawing Sheets

Figure 1:
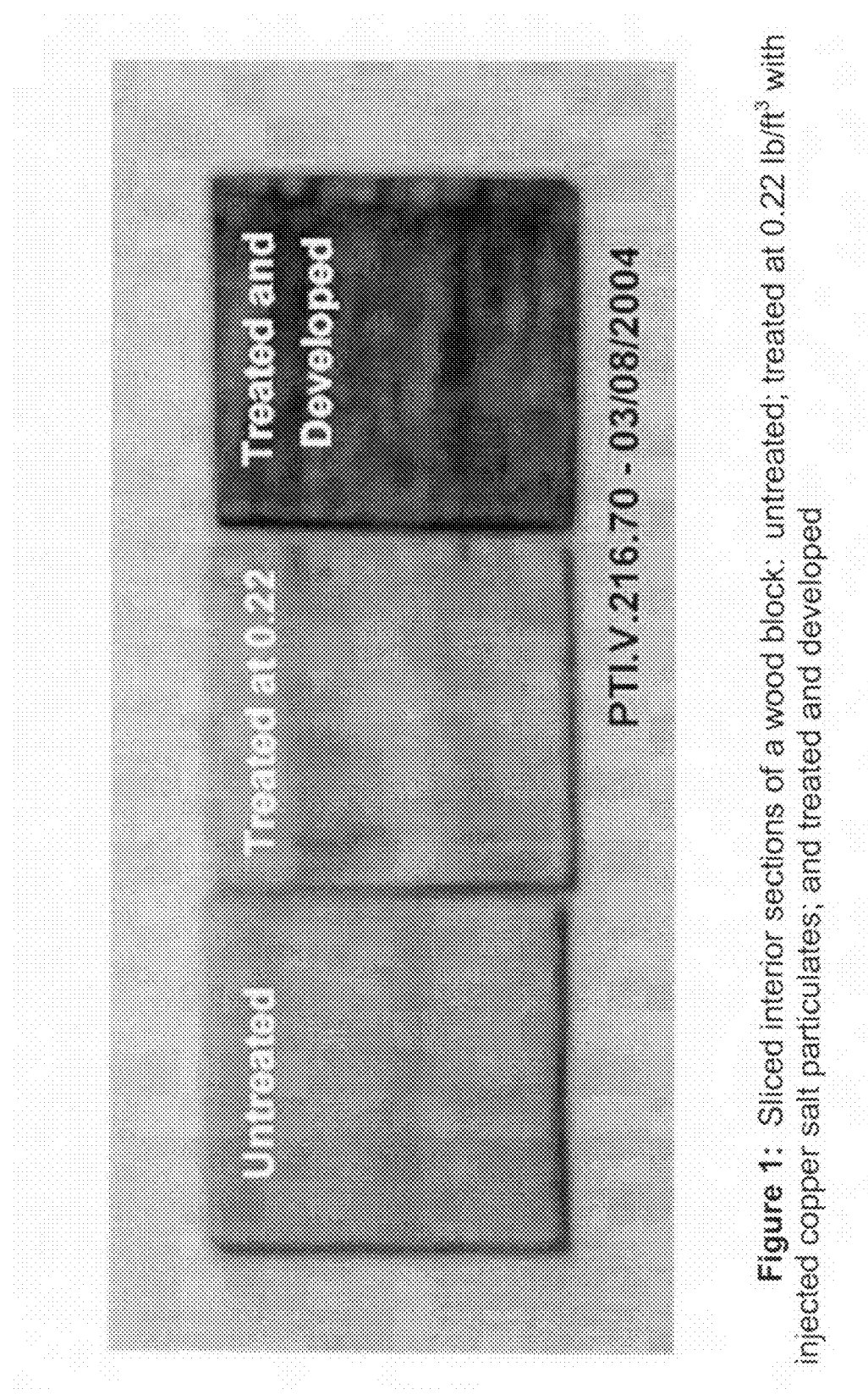

Figure 1: Sliced interior sections of a wood block: untreated; treated at 0.22 lb/ft$^3$ with injected copper salt particulates; and treated and developed Figure 2: AWPA leach rates

MILLED SUBMICRON CHLOROTHALONIL WITH NARROW PARTICLE SIZE DISTRIBUTION, AND USES THEREOF

CROSS-REFERENCE TO RELATED APPLICATIONS

This application claims priority to U.S. Provisional Application No. 60/616,646, filed on Oct. 8, 2004.

STATEMENT REGARDING FEDERALLY SPONSORED RESEARCH OR DEVELOPMENT not applicable

INCORPORATION-BY-REFERENCE OF MATERIAL SUBMITTED ON A COMPACT DISC not applicable

SEQUENCE LISTING not applicable

FIELD OF THE INVENTION

The present invention relates to a method of producing submicron-sized chlorothalonil particles, methods of packaging same, and uses thereof. More particularly, the invention relates to use of high density milling media having a diameter between 0.1 and 0.8 mm to provide unexpected Chlorothalonil particle size reduction and narrow particle size distribution. This chlorothalonil product is therefore useful in particulate form for direct injection into wood, for use in non-fouling paints, and for use in foliar applications at a reduced treatment quantity than was useful for prior art formulations.

BACKGROUND OF THE INVENTION

The efficient use of organic pesticides is often restricted by their inherent poor water-solubility.

Generally, these water-insoluble organic pesticides can be applied to a site or substrate in three ways: 1) as a dust, 2) as a solution in an organic solvent or a combination of water and one or more organic solvents, or 3) as an emulsion that is prepared by dissolving the product in an organic solvent, then dispersing the solution in water. All of these approaches have drawbacks. Application of a dust is associated with drift, poses a health hazard, and is inefficient. Solutions and emulsions that require an organic solvent are undesirable, since the solvent serves no other purpose but to act as a carrier for the product. As such, the solvent adds an unnecessary cost to the formulation and is an added health risk. Finally, emulsions are generally unstable and must be prepared at point of use, typically in the hours or minutes before use, and minor changes in the formulation, for example by addition of another biocide, may cause the emulsion to break and separate.

The low water solubility is also a factor at point of use. Generally, for low solubility fungicides, the amount of a fungicide needed to protect against various pests is generally dependent on the number of particles in a unit area. If 100 particles are needed on a leaf, and if the particle diameter is reduced to one third of the former diameter, then the dosage can theoretically be reduced to about 11% of the former dosage, resulting in lower cost, less pesticide residue on harvested crops, and mitigation of environmental impact.

It is known to mill certain organic pesticides. For instance, published U.S. Patent Application No. 2001/0051175 A1 describes milling large classes of fungicides with grinding media of substantially spheroidal shaped particles having an average size of less than 3 mm, and teaches that "suitable media material include [s] ZrO stabilized with magnesia, zirconium silicate, glass, stainless steel, polymeric beads, alumina, and titania, although the nature of the material is not believed to be critical." We believe these inventors were incorrect in their assumption that the grinding material and size were of little importance.

On the other hand, when a breakthrough is made, the product can be very successful. Copper (on a copper metal basis) is generally used as a biocidal agent (depending on crop, application, and activity) at application rates of 0.25 lb to 7.5 lbs per acre. Another biocide is copper hydroxide, which is a preferred low solubility copper salt, and which has >60% by weight copper and a solubility product constant of about $2 \times 10^{-20}$. Several years ago, copper hydroxide used for foliar applications had a particle size of about 1 to 3 microns. Then, a new product, Champ DP®, commercially available from Nufarm Americas, was made available with a median particle size of about 0.2 microns. This product was useful at half the application rate on a variety of crops, and the duration of treatment was not appreciably different than that of the products containing larger particles.

This is not to say that all biocides, even all low solubility fungicides, benefit from smaller size. For example, the ubiquitous elemental sulfur is generally advantageously 3 to 5 microns in diameter when used in foliar applications. While smaller particles can be formed, the actions of the atmosphere, moisture, and sunlight combine to eliminate the efficacy of the sulfur particles in too short a time to be of commercial interest. Additionally, particle size reduction below certain values (which depend on the product characteristics) can in the past only be achieved through expensive and elaborate procedures, and such procedures quickly price the product out of the market.

Chlorothalonil is commercially available as a suspension having an average particle size diameter between about 2 and about 5 microns. It is known to mill chlorothalonil, but no milling process had ever achieved a reduction in the $d_{50}$ (the volume average diameter) below about 2 microns. Backman et al. found that, within the limits tested, the efficacy of Chlorothalonil tended to increase with decreasing particle size and with increasing milling. Beckman tested standard air milled chlorothalonil with wet-milled chlorothalonil. The particle sizes tested are represented below, where the air milled product is the standard, and the hours of wet milling are provided, where "med. µ" is the median diameter in microns (NOT the $d_{50}$—the d50 will always be much higher than the median diameter), "<1µ, %" is the percentage of particles with a diameter less than 1 micron, and Def(0.42) is the defoliation of Florunner peanuts treated with the amount in parentheses, e.g., 0.42, in kg chlorothalonil per ha, where defoliation was presumed due top leafspot infestation:

| Type | Mill Time | med. µ | <1µ, % | Def (0) | Def (0.42) | Def (0.84) | Def (1.26) |
|---|---|---|---|---|---|---|---|
| 1974 data | | | | | | | |
| Air | — | 3.3 | 7% | — | 39 | 25 | 19 |
| Wet | 3 hr | 3.8 | 8% | — | 33 | 24 | 15.5 |
| Wet | 9 hr | 1.75 | 22% | — | 32 | 17.2 | 14.1 |
| Wet | 13 hr | 1.6 | 24% | — | 27 | 23 | 15.4 |

-continued

| Type | Mill Time | med. μ | <1μ, % | Def (0) | Def (0.42) | Def (0.84) | Def (1.26) |
|---|---|---|---|---|---|---|---|
| | | | 1975 data | | | | |
| Air | — | 3.3 | 5% | 39 | 35 | 34 | 27 |
| Wet | 3 hr | 3.7 | 10% | 39 | 35 | 28 | 28 |
| Wet | >9 hr | 1.6 | 22% | 37 | 32 | 29 | 29 |

This data generally show that the efficacy of the treatment generally increased with wet milling over air milling, and that the efficacy increased with milling time for the lowest treatment rate, though the data was not conclusive as the efficacy went down with increased milling time at the two higher treatment rates. See Backman, P. A., Munger, G. D., and Marks, A. F., The Effects of Particle Size and Distribution on Performance of the Fungicide Chlorothalonil, Phytopathology, Vol. 66, pages 1242–1245 (1976).

U.S. Pat. No. 5,360,783, the disclosure of which is incorporated herein by reference, particularly noting the milling method and the dispersants and stabilizers disclosed therein, discloses in Example 2 milling Maneb with 2 mm glass beads. The resulting mean particle diameter of the Maneb was 1.7–1.8 micons. Also in this patent, chlorothalonil (Daconil) was milled in the same manner in Test 5, and the resulting average particle size diameter was 2.3 microns.

U.S. Pat. No. 5,667,795, the disclosure of which is incorporated herein be reference, particularly relating to the adjuvants, describes milling 40% chlorothalonil, 5.6% zinc oxide, 6% PLURONIC P-104 (a poly (oxypropylene) block copolymer with poly (oxyethylene), commercially available from BASF), 0.25% xanthan gum (commercially available from Kelco), 0.25% Antifoam FG-10 (silicon emulsion, commercially available from Dow Corning), 1% HI-SIL 233 (precipitated amorphous silica, commercially available from PPG Ind.), 0.4% PVP K-30 (poly(vinyl pyrrolidone), commercially available from BASF), 3% propylene glycol, 0.1% PROXEL GXL (1,2-benzisothiazolin-3-one, commercially available from ICI); 1.5% EDTA, and balance water in a wet mill or high speed media mill. This patent does not describe the milling media, but states the average particle size of the product was 3 microns.

Curry et al. at International Specialty Products have ground a few biocides with 0.1 cm zirconia at 70% to 80% loading. For instance, U.S. Published Patent Application Nos. 2004/0063847 A1 and 2003/0040569 A1 describe milling metaldehyde with a variety of surfactants and dispersants, milling at 0–5° C., and recycling the material at 19 passes per minute for 10 minutes. Fine suspensions were produced with particle size distributions in which 90% of the particles had a diameter less than 2.5 microns, and in which the mean volume diameter was less than 1.5 microns. A chlorothalonil suspension was described as being milled in the same manner, but data on particle size was not reported. However, commonly-assigned U.S. Published Patent Application No. 2004/0024099 A1 described an example where a composition of chlorothalonil was wet milled under the same conditions described above, i.e., a 70% to 80% loading of 0.1 cm zirconium (sp) beads at 3000 rpm for 10 minutes with 19 recycles per minute. The resulting compositions contained 41% chlorothalonil and a variety of surfactants and dispersants. The milling temperature jacket was 0° C., and the milled material was 15–21° C. The publication claims that 90% of the number of particles had a size below 0.5 microns but that the mean volume diameter ($d_{50}$) was "less than 3 microns", meaning half the volume of particles had particle sizes greater than "less than 3 microns." The art uses the term "less than" to denote the maximum mean diameter in a series of tests, but it is well known in the art that routine changes in parameters such as milling time will not appreciably change the mean volume diameter, as discussed infra. The resulting chlorothalonil material made according to the International Specialty Products process thus has a mean volume diameter $d_{50}$ of 2 to 3 microns. This is consistent with the other disclosures.

The phenomena of a wide particle size distribution should be clarified. The International Specialty Products inventors described their chlorothalonil composition as having 90% of particles below 0.5 microns, but as having a mean volume diameter in the range of 2–3 microns. This wide particle size distribution is common, and it severely limits the benefits of the low particle size product, e.g., when used in paints, wood preservatives, and foliar applications.

For example, in co-pending and commonly-owned U.S. patent application Ser. No. 10/868,967 filed Jun. 17, 2004, we discussed how particles up to 0.5 microns in diameter were injectable into wood. The mean volume diameter of Champ DP®, a small diameter copper salt product, was 0.2 microns. Therefore, one might expect this material to be readily injectable into wood. However, while 57% by weight of particles of copper hydroxide in a particular lot of Champ DP® was 0.2 microns or smaller, when we tried to inject this material into wood this Champ DP® material plugged the surface of the wood and would not penetrate into the wood matrix. We discovered the reason was that there was a critical fraction of particles having a diameter greater than about 1 micron. This critical fraction of material was believed to bridge pores in the wood, and, once the pores were bridged, substantially all the remaining particles, including those having a diameter less than 0.2 microns, subsequently plated on the wood surface.

Further, extended grinding times using milling media routinely used in the art 1) will not provide a more uniform product, and 2) will not significantly lower the $d_{50}$. It is known that compounds can be reduced to a particular particle size distribution, where further milling with that media has virtually no effect. For example, we milled the Champ DP® material described above (having a d50 of 0.2 microns, but a $d_{95}$ over a micron) for two days using 2 mm zirconia beads as the media, and the injectability and particle size distribution of the resultant composition was essentially unchanged. Along those lines, U.S. Published Patent Application No. 2004/0050298 A1, in the unrelated art of formulating pigments, discloses that wet milling in a pearl mill with mixed zirconium oxide balls having a diameter of from 0.1 to 0.3 mm could provide a desired product in 20 to 200 minutes, but that longer milling periods had no significant effect on the properties of the product, and that "as a result, the risk of overmilling can be excluded, with very great advantage for the meeting of specifications, especially if it is ensured that the radial speed of the mill is not too high."

U.S. Published Patent Application No. 2002/0047058 A1, which relates to preparing certain pharmaceutical formulations, discusses milling the pharmaceuticals with 0.5 mm diameter zirconium (sp) media to obtain pharmaceutical formulations having particle diameters less than 0.5 microns. In addition, U.S. Published Patent Application No. 2004/0051084 A1 describes manufacturing polymer particles comprising recurring thiophene units and polystyrenesulfonic acid by oxidative polymerization of ethylenedioxythiophene in the presence of polystyrenesulfonic acid and subsequent milling with 0.5 mm diameter zirconia.

Further, U.S. Published Patent Application No. 2002/0055046 A1 describes milling titanium dioxide with zirconia beads which have a diameter of 0.5 mm (manufactured by Nikkato Co., Ltd), where the resultant mean particle diameter of the titanium dioxide was 2.5 microns. Also, several published applications relate to milling photographic compositions with a 0.5 mm zirconia media.

While it is known to grind certain materials to smaller size, certain biocides are particularly resistant to grinding to less than 1 micron diameter. What is needed in the art is a process whereby a wide variety of biocides can be readily milled to a particle size distribution where $d_{50}$ is less than 1 micron, preferably less than 0.7 microns.

The lowest $d_{50}$ obtainable from grinding with a particular media will depend on the properties of material being ground. Several biocides can purportedly be milled to a $d_{50}$ below about 1 micron, and occasionally below 0.5 micron. These biocides therefore have physical properties that differ from those of chlorothalonil, making them easier to grind than chlorothalonil. For example, it has been reported that milling triphenyltin acetate, 1-methyl-3-(2-fluoro-6-chlorophenyl)-5-(3-methyl-4-bromothien-2-yl)-1H-1,2,4-triazole, Spinosad insecticide, epoxiconazole, chlorpyrifos, and certain other materials to sub-micron size using milling materials that are outside the scope of this invention (see, e.g., U.S. Published Patent Application No. 2001/0051175 A1). However, we believe that using the method of this invention will provide a narrower particle size distribution than the prior art milling methods.

What is needed in the art is a process whereby a wide variety of biocides can be readily milled to a particle size distribution where $d_{90}$ is less than 1 micron, preferably less than 0.7 microns.

Mentioning a reference in this background section is explicitly not a concession that such reference constitutes prior art under the patent laws of any country in which this application is pending. We found no reference in the published applications which relates to milling a sparingly soluble inorganic biocidal compound, for example copper hydroxide, with 0.5 mm zirconia. We found no reference in the published applications which relates to milling an organic fungicide with 0.5 mm zirconia media. We, in particular, found no reference in the published applications which related to milling chlorothalonil with 0.5 mm zirconia media. It would be an advantage in the art to provide a pesticide formulation of fairly uniformly sized submicron organic pesticide particles. It would be an advantage in the art to provide a method to routinely and predictably: 1) prepare a pesticide formulation of fairly uniformly sized submicron organic pesticide particles; 2) a pesticide formulation of fairly uniformly sized submicron organic pesticide particles with sub-micron sparingly soluble inorganic biocidal particles; and 3) a method of manufacturing the aforesaid formulations that will allow the formulation to have commercial application in the fields of a) foliar applications, b) wood preservative treatments, c) turf applications, and d) non-fouling paints and coatings.

SUMMARY OF THE INVENTION

One of the key aspects of the present invention is not just attaining smaller particles but also rendering the particles fairly uniform. Any grinding of a partially crystalline material will produce some small fraction of sub-micron particles.

A principal aspect of this invention is providing a method of producing a chlorothalonil product where the $d_{50}$ is below 1 micron, preferably below 0.7 microns, and for certain applications, below 0.4 microns, for example between about 0.1 microns and about 0.3 microns.

For foliar applications, another principal aspect of this invention is providing a method of producing the above products where the $d_{90}$ is less than about 4 times the $d_{50}$, preferably less than three times the $d_{50}$; where the $d_{10}$ is advantageously greater than about ¼th the $d_{50}$, preferably greater than about ⅓rd the $d_{50}$.

For wood preservation applications, another principal aspect of this invention is providing a method of producing a each of the above products where the $d_{98}$, preferably the $d_{99}$, is less than about 4 times the $d_{50}$, preferably less three times the $d_{50}$.

A first aspect of the invention is a method of preparing a organic biocide product having a $d_{50}$ equal to or less than about 1 micron, comprising the steps of: 1) providing the solid organic biocide, and a liquid comprising a surface active agent, to a mill; providing a milling media comprising an effective amount of milling beads having a diameter between 0.1 mm and 0.8 mm, preferably between about 0.2 mm and about 0.7 mm, more preferably between about 0.3 mm and about 0.6 mm, wherein these milling beads have a density greater than about 3 grams/cm3, preferably equal to or greater than 3.5 grams/cm3, more preferably equal to or greater than 3.8 grams/cm3, most preferably equal to or greater than 5.5 grams/cm3, for example a zirconia bead having a density of about 6 grams/cm3; and 2) wet milling the material at high speed, for example between 300 and 6000 rpm, more preferably between 1000 and 4000 rpm, for example between about 2000 and 3600 rpm, where milling speed is provided for a laboratory scale ball mill, for a time sufficient to obtain a product having a mean volume particle diameter of about 1 micron or smaller, for example between about 5 minutes and 300 minutes, preferably from about 10 minutes to about 240 minutes, and most preferably from about 15 minutes to about 60 minutes. As little as 5% by volume of the milling media need be within the preferred specifications for milling some materials, but better results are obtained if greater than 10% by weight, preferably greater than 25% by weight, for example between 40% and 100% by weight of the milling material is within the preferred specifications. For milling material outside the preferred specifications, advantageously this material has a density greater than 3 grams/$cm^3$ and a diameter less than 4 mm, for example 1 or 2 mm zirconia or zircionium silicate milling beads.

A second aspect of the invention is a method of preparing a solid organic biocide product, e.g., chlorothalonil, comprising the steps of: 1) providing the solid organic biocide to a mill, and 2) milling the material with a milling media, wherein at least 25% by weight of the milling media has a density equal to or greater than 3.8 and a diameter between 0.1 and 0.7 mm.

The milling media need not be of one composition or size. Further, not all the milling material need be the preferred material, i.e., having a preferred diameter between 0.1 mm and 0.8 mm, preferably between 0.2 mm and 0.7 mm, more preferably between 0.3 mm and 0.6 mm, and having a preferred density equal to or greater than 3.8 grams/$cm^3$, preferably greater than or equal to 5.5 grams/$cm^3$, more preferably greater than or equal to 6 grams/$cm^3$. In fact, as little as 10% of this media will provide the effective grinding. The amount of the preferred milling media, based on the total weight of media in the mill, can be between 5% and 100%, is advantageously between 10% and 100%, and is preferably between 25% and 90%, for example between about 40% and 80%. Media not within the preferred cattegory can be somewhat larger, say 1 mm to 4 mm in diameter, preferably from 1 mm to 2 mm in diameter, and advantageously also has a density equal to or greater than 3.8 grams/cm$^3$. Preferably at least about 10%, preferably about 25%, alternately at least about 30%, for example between about 50% and about 99%, of the media has a mean diameter of between about 0.1 mm to about 0.8 mm, preferably between about 0.3 mm and about 0.6 mm, or alternatively between about 0.3 mm and about 0.5 mm. The remaining media (not within the specified particle size) can be larger or smaller, but, in preferred embodiments, the media not within the specified size is larger than the media in the specified size, for example at least a portion of the milling media not within the preferred size range(s) has a diameter between about 1.5 and about 4 times, for example between about 1.9 and about 3 times, the diameter of the preferred media. A preferred media is 0.5 mm zirconia, or a mixture of 0.5 mm zirconia and 1–2 mm zirconia, where at least about 25% by weight of the media is 0.5 mm zirconia. The remaining media need not comprise zirconium, but advantageously will have a density greater than 3.5 g/cc. Using media comprising a zirconia portion and a steel portion can be advantageous.

A third aspect of the invention is a method of preparing a submicron organic biocide product, e.g., chlorothalonil, comprising the steps of: 1) providing the solid organic biocide and a liquid to a mill, and 2) milling the material with a milling media comprising a zirconium oxide having a diameter between about 0.1 mm and about 0.7 mm. The zirconium oxide can comprise any stabilizers and/or dopants known in the art, including, for example, cerium, yttrium, and magnesium.

A fourth aspect of the invention is a method of preparing a submicron organic biocide, e.g., chlorothalonil, product comprising the steps of: 1) providing the solid organic biocide and a liquid to a mill, and 2) milling the material with a milling media comprising a zirconium silicate having a diameter between about 0.1 mm and about 0.7 mm and a density greater than about 5.5 grams per cubic centimeter.

A fifth aspect of the invention is a method of preparing a submicron chlorothalonil product comprising the steps of: 1) providing the chlorothalonil to a mill, and 2) milling the material with a milling media comprising a zirconium oxide having a diameter between about 0.1 mm and about 0.7 mm. The invention also encompasses a chlorothalonil product having a $d_{50}$ below about 1 micron, preferably below about 0.5 microns, which advantageously also exhibits a $d_{90}$ that is less than about three times the $d_{50}$, preferably less than about two times the $d_{50}$. In one embodiment, the chlorothanonil product has a mean volume particle diameter $d_{50}$ of between about 0.05 and about 1 micron, and a $d_{90}$, such that 90 volume percent of the product has a diameter of the $d_{90}$ or less, of less than 2 microns, and further the chlorothalonil product has a $d_{96}$, such that 96 volume percent of the product has a diameter of the $d_{96}$ or less, is less than about 0.6 microns. In one embodiment, the chlorothanonil product has a mean volume particle diameter $d_{50}$ of between about 0.1 and about 0.3 micron, and a $d_{90}$, such that 90 volume percent of the product has a diameter of the $d_{90}$ or less, of less than 2 microns, and further the chiorothalonil product has a d98 of less than about 0.4 microns.

A sixth aspect of the invention is a method of preparing a submicron organic biocide, e.g., chlorothalonil, product for use as an injectable particulate wood preservative, comprising the steps of: 1) providing the organic biocide to a mill, and 2) milling the material with a milling media having a density greater than about 3.5 and having a diameter between about 0.1 mm and about 0.7 mm. The invention also encompasses injecting the composition, which may be admixed with one or more injectable particulate sparingly soluble biocidal salts.

Another key aspect of the invention is to make a variety of biocidal particulate slurries available that are injectable into wood, thereby serving as a particulate wood preservative. Requirements of injectability into wood for substantially round, e.g., the diameter is one direction is within a factor of two of the diameter measured in a different direction, such as would be found in milled particles, are:

1) the $d_{96}$ is equal to or less than about 1 micron, but is preferably about 0.7 microns or less, more preferably about 0.5 microns or less, for example equal to or less than about 0.3 microns, or equal to or less than about 0.2 microns;

2) the $d_{99}$ is equal to or less than about 2 microns, preferably equal to or less than 1.5 microns, more preferably equal to or less than about 1 micron; and 3), the $d_{50}$ is less than 0.5 microns, preferably less than 0.4 microns, and the $d_{50}$ is greater than 0.02 microns, more preferably greater than 0.05 microns, for example a slurry where the $d_{50}$ is between about 0.1 microns and about 0.3 microns. We believe the first criteria primarily addresses the phenomena of bridging and subsequent plugging of pore throats, the second criteria addresses the phenomena of forming a filter cake, and the third criteria addresses the issue of having particulates disposed in the wood which have an optimum size to ensure the treatment has an acceptable bio-activity and lifetime. Once a pore throat is partially plugged, complete plugging and undesired buildup generally quickly ensues.

A seventh aspect of the invention is a method of preparing a submicron organic biocide, e.g., chlorothalonil, product for use as a foliar treatment, or as an additive in paints or coatings, comprising the steps of: 1) providing the organic biocide to a mill, and 2) milling the material with a milling media having a density greater than about 3.5 and having a diameter between about 0.1 mm and about 0.7 mm. The density of the milling media, and especially of the milling media within the size range 0.3 to 0.7 mm, is advantageously equal to or greater than 3.5, preferably equal to or greater than about 3.8, for example greater than about 4, preferably greater than about 5.5, for example equal to or greater than about 6 grams per cubic centimeter. Ceramic milling media is preferred over metallic milling media.

The invention also encompasses a milled organic biocide product from any of the above aspects and having a $d_{50}$ below about 1 micron, preferably below about 0.5 microns, and in many cases below about 0.3 microns, and which further may advantageously have a $d_{90}$ that is less than about three times the $d_{50}$, preferably less than about two times the $d_{50}$. The invention also encompasses a organic biocide product from any of the above aspects and having a $d_{50}$ below about 1 micron, preferably below about 0.5 microns, for example below about 0.3 microns, which further has a $d_{95}$ that is less than about 1.4 microns, preferably less than about 1 micron, for example less than about 0.7 microns. In each embodiment, the milling load is preferably about 50% of the volume of the mill, though loadings between 40% and 80% are efficient. In each embodiment, advantageously water and surface active agents are added to the product before or during milling. In each embodiment, the product can be transported as a stable slurry, as a wettable powder, or as granules that disintegrate on mixing with water to release the product.

In each embodiment, the milled particulate organic biocide, e.g., chlorothalonil, may be combined with another milled inorganic particulate biocide, which may be a sparingly soluble biocidal salt such as copper hydroxide, zinc hydroxide, and/or basic copper carbonate, or a substantially insoluble biocidal oxide, such as Copper(I) oxide and/or zinc oxide, or any combinations thereof, wherein the other particulate biocide advantageously also has a $d_{50}$ below about 1 micron, advantageously below about 0.5 microns. Alternatively, the second biocide may be a milled organo-metallic particulate biocide, or another milled organic particulate biocide.

When combining a plurality of particulate biocides into a slurry, it is advantageous to make the dispersants and surfactants be compatible one with another. Using anion dispersants on a first biocide and cationic dispersants on the second biocide can result in undesired interactions when the slurry is prepared.

The literature is full of inventions where two or more biocides have a synergistic effect. Often, this is the result of the second biocide protecting the first biocide against organisms that can degrade the first biocide. For sparingly soluble or substantially insoluble biocides, such synergy can only be achieved if both biocides are in the area to be protected. As a result, assuming relatively equal amounts of biocide, the two sparingly soluble or insoluble biocides should be relatively comparable in size to achieve the distribution needed for effective synergy.

In some instances the second biocide is present in or as an organic liquid. In such cases, the organic liquid can be solubilized in solvent, emulsified in water, and then added to the first biocide before or during milling, or less preferably after milling. The surface of the first biocide can be made compatible with the organic phase of the emulsion, and the liquid or solvated biocide can coat the primary particles. Advantageously, solvent can be withdrawn, for example by venting the gases above the biocidal composition or by drawing a vacuum. The liquid biocide will subsequently be bound to the surface of the particulate biocide. Not only does this have the advantage of providing the two biocides in close contact so synergy will be observed, but also this provides a method for broadcasting the liquid emulsion without exposing field personnel (if the composition is for foliar applications), painters (if the composition is for non-fouling paints or coatings), and wood preservation personnel from exposure to potentially harmful solvents. Advantageously, the particulate biocidal composition, be it slurry, wettable powder, or granules, can be substantially free of volatile solvents.

The present invention also encompasses methods of using the products of the above described processes, which include: injecting the particulate product of any of the processes described herein into wood if the composition is a wood preservative; spreading the particulate product of any of the processes described herein over crops, if the composition is used as a foliar biocide; or mixing the particulate product of any of the processes described herein into a paint or coating formulation to impart biocidal properties to the paint or coating.

BRIEF DESCRIPTION OF THE FIGURES

FIG. 1 depicts three comparative photographs of a sliced interior section of a wood block. From left to right: untreated wood; wood treated with particulate copper hydroxide of the present invention; and development of the wood shown in the second paragraph with dithio-oxamide/ammonia to show the penetration of the injected particulate copper hydroxide. The stain corresponds to copper and indicates that the copper is evenly dispersed throughout the wood.

FIG. 2 depicts exemplary leaching data in wood treated with various particulate slurries. Measurement of leaching followed the AWPA Standard Method E11-97. The treatments are as follows: tebuconazole (TEB) and injected basic copper carbonate (BCC) particulates; traditionally chromated copper arsenate (CCA)-treated wood (as a control); TEB and copper methanolamine carbonate (as a control, believed to approximate the currently available Wolman E treatment); TEB and injected BCC particulates with sodium bicarbonate buffer; injected BCC particulates; TEB and injected copper hydroxide particulates modified with zinc and magnesium; about 5% TEB and injected copper hydroxide particulates modified with phosphate coating; TEB and injected tribasic copper sulfate particulates; and TEB and injected copper oxychloride particulates.

FIG. 3 depicts representative comparative photographs showing wood treated with copper hydroxide particulates having a $d_{50}$ of 2.5 microns (which unacceptably plugged the wood, resulting in an unsightly blue-green stain); and wood treated with copper hydroxide particulates milled according to the process of the described invention (resulting in wood having a clean appearance).

DETAILED DESCRIPTION OF THE PREFERRED EMBODIMENTS

Unless otherwise specified, all compositions are given in percent, where the percent is the percent by weight based on the total weight of the entire component, e.g., of the particle, or to the injectable composition. In the event a composition is defined in "parts" of various components, this is parts by weight, such that the total number of parts in the composition is between 90 and 110.

As used herein, the terms "biocide" and "pesticide" are used interchangeably to mean a chemical agent capable of destroying living organisms, both microscopic and macroscopic, and not merely "pests."

As used herein, the term "sparingly soluble" as it applies to inorganic salts is meant to include salts with a $K_{sp}$ in pure water of between about $10^{-12}$ to about $10^{-24}$ for salts with only one anion, and from about $10^{-14}$ to about $10^{-27}$ for salts with two anions. Preferred inorganic biocidal salts include copper salts, zinc salts, and tin salts, or combinations thereof. In other embodiments, inorganic biocidal salts can include silver salts. The most preferred inorganic biocidal salts are copper salts. Preferred sparingly soluble copper salts include copper hydroxide, basic copper carbonate, basic copper chloride (copper oxychloride), and basic copper sulfate. The most preferred inorganic copper salts are copper hydroxide and basis copper carbonate.

One aspect of this invention is a method of making small particles of organic biocide. Although U.S. Published Patent Application No. 2001/0051175 A1 teaches that the nature of the material is not believed to be critical, it has surprisingly been discovered that grinding media containing zirconium atoms are particularly preferable in milling methods according to the invention. In addition, while not wishing to be bound by theory, it is hypothesized that using grinding media having a sub-millimeter average particle size is necessary to achieve the desired sub-micron particle size for many difficult-to-mill biocides, e.g., chlorothalonil. The particles can be milled/ground at any suitable processing temperature where the agricultural product is stable. Typically, processing temperatures are not greater than the boiling point of water and not greater than the melting point of the solid, but ambient temperature or only slight heating or cooling is preferred. In several preferred embodiments, particularly those where the organic biocide is chlorothalonil, the volume mean particle diameter is less than about 1 micron, more preferably less than about 400 nm, and most preferably less than about 300 nm.

Particle size as used herein is the mean weight average particle diameter, which is equivalent to the mean volume average particle diameter, also known as $d_{50}$. For larger particles this "average" value can be determined from settling velocity in a fluid, which is a preferred method of measuring particle size. Unless otherwise specified, as used herein the biocide particle diameter is given as the $d_{50}$ mean volume average diameter. The $d_{xx}$ is the diameter where the subscript "xx" is the percent of the volume of the solid material that has an average diameter smaller than the stated diameter. Other key parameters, such as $d_{80}$, $d_{95}$, and $d_{99}$, are similarly defined and are useful for various applications where not only is the mean volume particle diameter important but also the amount of larger particles (the size distribution, especially in the higher particle diameter range). Particle diameter can be beneficially determined by Stokes Law settling velocities of particles in a fluid, for example with a Model LA 700 or a CAPA™ 700 sold by Horiba and Co. Ltd., or a Sedigraph™ 5100T manufactured by Micromeritics, Inc., which uses x-ray detection and bases calculations of size on Stoke's Law, to a size down to about 0.2 microns. Smaller sizes are beneficially determined by for example a dynamic light scattering method, preferably with a Coulter™ counter, or with a laser scattering method, or electron microscopy.

The preferred organic biocides for use with this invention include those organic biocides that are substantially insoluble, or are only sparingly soluble, in water, and also which are substantially stable against weathering. The reason is that the smaller particles of this invention must be sufficiently bioactive and must last a commercially acceptable time. For sparingly soluble organic biocides, enhanced bioactivity may be obtained due to the greater allowable coverage (number of particles) and tenacity associated with smaller particles, as opposed to larger particles of the same organic biocide. Enhanced bioactivity is a significant factor, as it allows the use of less biocide in an application.

By substantially insoluble (or "sparingly soluble", as the term relates to organic biocides), we mean the organic biocide has a solubility in water of less than about 0.1%, and most preferably less than about 0.01%, for example in an amount of between about 0.005 ppm and about 1000 ppm, alternatively between about 0.1 ppm and about 100 ppm or between about 0.01 ppm and about 200 ppm. It should be understood that the water solubilities of many pesticides are pH-dependent, as a result of the functional groups they contain. Thus, biocides with carboxylic acid groups or with sulfonamide or sulfonylurea groups, for example, may meet the low solubility requirements at low pH but may be too highly soluble at higher pH values. The pH of the aqueous dispersion can be adjusted to ensure substantial insolubility, or at least sparing solubility, of these biocides.

The organic biocide beneficially has a half life in water from about pH 3 to about pH 11 of at least about 2 days, preferably at least about one week. The organic biocide beneficially is resistant to photolysis by sunlight. By "resistant to photolysis," we mean that particles having an average diameter of about 0.3 to about 0.5 microns will maintain at least 50% of their activity, measured against the target organism, after exposure to about 12 hours per day of sunlight at about 75% humidity and ambient temperature for 14 days. Finally, the organic biocide should be substantially non-volatile at ambient conditions, by which we mean that weight of the particles used in the above described test for photolysis should, at the end of the test, be within about 20% of the weight of the particles before the test began.

While it is not related to the performance of the particulate product, the preferred organic biocides are crystalline or semi-crystalline and have a melting temperature in excess of 100° C. Such properties tend to simplify the milling process.

Generally, the processes of this invention produce slurries or suspensions of particulate biocidal material where the particle size distribution, in various embodiments, has the following characteristics: A) a volume mean diameter, $d_{50}$, of less than about 1 micron and a $d_{90}$ of less than about 2 microns; B) a volume mean diameter, $d_{50}$, of less than about 0.6 micron and a $d_{90}$ of less than about 1.4 microns, preferably less than about 1 micron; C) a volume mean diameter, $d_{50}$, of less than about 0.4 micron and a $d_{90}$ of less than about 1 micron, preferably less than about 0.7 microns; and/or D) a volume mean diameter, $d_{50}$, between about 0.1 and 0.3 microns and $d_{90}$ that is less than about 3 times the $d_{50}$. The preferred processes can provide a tighter control on particle size, e.g., a particulate organic biocide composition having a $d_{50}$ less than about 1 micron, preferably less than about 0.5 microns, having a $d_{90}$ less than about twice the $d_{50}$, and optionally having a $d_{10}$ greater than about one half the $d_{50}$. Even more preferably, the preferred processes can provide a particulate organic biocide composition having a $d_{50}$ less than 1 micron, preferably less than 0.5 microns, having a $d_{95}$ less than about twice the $d_{50}$, and optionally having a $d_5$ greater than about one half the $d_{50}$.

Such tight particle size distributions is beneficial in all applications and can be as important as, if not more important than, the mean particle size. The examples in U.S. Published Patent Application No. 2004/0063847 A1 shows why this is so. For sparingly soluble and essentially insoluble biocides, protection depends on having a particle of the biocide within a particular area or volume of the substrate to be protected. The longevity of any particle, the rainfastness of any particle, and the suspendability of any particle are all functions of the particle diameter.

The U.S. Published Patent Application No. 2004/0063847 describe a chlorothalonil suspension having a distribution such that 90% of the particles have a diameter less than 0.5 microns and having a $d_{50}$ of "less than 3 microns" (meaning between 2 and 3 microns). Hypothetically, this chlorothalonil suspension can have 95 particles with 0.4 microns particle diameter for every 5 particles with 2.4 microns particle diameter. The mass of each of the larger particles is larger than the mass of all 95 of the smaller particles combined, and the 5 larger particles constitute about 91% of the total biocide in the formulation. The bigger particles do not protect a significantly larger area of for example a leaf than does the smaller particles. In such a scenario, if a leaf requires 100 biocide particles, it will, on average, get 95 small particles and 5 large particles of biocide. The amount of biocide, for example in pounds per acre, needed to obtain the 100 particles is over 12 times the amount if all 100 particles were smaller particles. Also, such a composition could not be injected into wood, as the large particles would plug the surface of the wood and make unsightly stains, and the homogeneity of the penetration would be compromised. In addition, such a composition would make an unsightly coating of paint, as the large particles of biocide would disrupt the thinner coating of pigment. Further, for foliar applications, the larger particles are much more susceptible to being washed from the surface than are smaller particles, so in a short time as much as 91% of the biocide mass may be washed away.

If, on the other hand, the $d_{90}$ is within a factor of two of the $d_{50}$ and the $d_{50}$ is, for example, 0.4 microns, then the situation changes radically. Such a composition may be simplified to a composition having 95 particles of 0.4 microns diameter, and about two particles with diameter of 0.8 microns. In this case, the larger particles will have rainfastness closer to the smaller particles, the larger particles would be injectable into wood, and less than 10–20% of the mass of the biocide will be in the larger particles. For these many reasons, having a narrow particle size distribution is desirable.

While generally not necessary, the particle size distribution of the product of this invention can be further narrowed, for example, by sedimentation or by filtering or centrifuging the suspension at a speed such that substantially all particles less than a certain size are removed. While a fraction of the particles may be lost to the recycling process by such a refinement, this may be preferable if the desired particle size distribution can not otherwise be achieved.

Many biocides can not be reduced to particle size $d_{50}$ less than about 1 micron and $d_{90}$ less than about 2 times $d_{50}$ when grinding with conventional media, e.g., 1 mm zirconia, 2 mm steel balls, and the like, at commercially acceptable milling speeds. These biocides will particularly benefit from the process of this invention, as the material and procedures described here will allow commercial production and use of products having biocide particulates with a size distribution $d_{50}$ less than about 0.7 microns and $d_{90}$ less than about 2 times $d_{50}$. Such biocides are known generally in the art.

Biocides include herbicides, insecticides, and fungicides, and, particularly important where woods are the substrate, moldicides. Examples of classes of compounds that have insecticidal activity and meet the solubility (and optionally also the crystallinity and melting point) requirements include, but are not restricted to, benzoyl ureas such as hexaflumuron, diacylhydrazines such as tebufenozide, carbamates such as carbofuran, pyrethroids such as alpha-cypermethrin, organophosphates such as phosmet, triazoles, and natural products such as spinosyns.

Examples of classes of compounds that have herbicidal activity and meet the solubility (and optionally also the crystallinity and melting point) requirements include, but are not restricted to, imidazolinones such as imazaquin, sulfonylureas such as chlorimuron-ethyl, triazolopyrimidine sulfonamides such as flumetsulam, aryloxyphenoxy propionates such as quizalofop ethyl, aryl ureas such as isoproturon and chlorotoluron, triazines such as atrazine and simazine, aryl carboxylic acids such as picloram, aryloxy alkanoic acids such as MCPA, chloroacetanilides such as metazachlor, dintroanilines such as oryzalin, pyrazoles such as pyrazolynate, and diphenyl ethers such as bifenox.

Examples of classes of compounds that have fungicidal activity and meet the solubility (and optionally also the crystallinity and melting point) requirements include, but are not restricted to, morpholines such as dimethomorph, phenylamides such as benalaxyl, azoles such as hexaconazole, strobilurins such as azoxystrobin, phthalonitriles such as chlorothalonil, and phenoxyquinolines such as quinoxyfen. A preferred class of materials for use in this process include the class of biocidal phthalimides, of which chlorothalonil is a prime example.

Additionally or alternately, other acceptable biocides can include, but are not limited to, diuron, chlorotoluron, simazine, atrazine, carbendazime, maneb, mancozeb, fentin hydroxide, endosulfan, and combinations thereof.

Additionally or alternately, other acceptable biocides can include, but are not limited to, amitraz, azinphos-ethyl, azinphos-methyl, benzoximate, fenobucarb, gamma-HCH, methidathion, deltamethrin, dicofol, dioxabenzafos, dioxacarb, dinobuton, endosulfan, bifenthrin, binapacryl, bioresmethrin, chlorpyrifos, chlorpyrifos-methyl, EPNethiofencarb, cyanophos, cyfluthrin, tetradifon, cypermethrin, tralomethrin, bromophos, N-2,3-dihydro-3-methyl-1,3-thiazol-2-ylidene-xylidene, 2,4-parathion methyl, bromopropylate, butacarboxim, butoxycarboxin, chlordimeform, phosalone, chlorobenzilate, phosfolan, chloropropylate, phosmet, chlorophoxim, promecarb, fenamiphos, quinalphos, resmethrin, temephos, pirimiphos-ethyl, tetramethrin, pirimiphos-methyl, xylylcarb, profenofos, acrinathrin, propaphos, allethrin, propargite, benfuracarb, propetamphos, bioallethrin, pyrachlofos, bioallethrin S, tefluthrin, bioresmethrin, terbufos, buprofezin, tetrachlorinphos, chlorfenvinphos, tralomethrin, chlorflurazuron, triazophos, chlormephos, pyrachlofos, tefluthrin, terbufos, tetrachlorinphos, cycloprothrin, betacyfluthrin, cyhalothrin, cambda-cyhalothrin, tralomethrin, alpha-cypermethrin, triazophos, beta-cypermethrin, cyphenothrin, demeton-S-methyl, dichlorvos, disulfoton, edifenphos, empenthrin, esfenvalerate, ethoprophos, etofenprox, etrimphos, fenazaquin, fenitrothion, fenthiocarb, fenpropathrin, fenthion, fenvalerate, flucythrinate, flufenoxuron, tau-fluvalinate, formothion, hexaflumuron, hydroprene, isofenphos, isoprocarb, isoxathion, malathion, mephospholan, methoprene, methoxychlor, mevinphos, permethrin, phenothrin, phenthoate, benalaxyl, biteranol, bupirimate, cyproconazole, carboxin, tetraconazole, dodemorph, difenoconazole, dodine, dimethomoph, fenarimol, diniconazole, ditalimfos, ethoxyquin, myclobutanil, etridiazole, nuarimol, fenpropidin, oxycarboxin, fluchloralin, penconazole, flusilazole, prochloraz, imibenconazole, tolclofos-methyl, myclobutanil, triadimefon, propiconazole, triadimenol, pyrifenox, azaconazole, tebuconazole, epoxyconazole, tridemorph, fenpropimorph, triflumizole, 2,4-D esters, diclofop-methyldiethatyl, 2,4-DB esters, dimethachlor, acetochlor, dinitramine, aclonifen, ethalfluralin, alachlor, ethofumesate, anilophos, fenobucarb, benfluralin, fenoxapropethyl, benfuresate, fluazifop, bensulide, fluazifop-P, benzoylprop-ethyl, fluchloralin, bifenox, flufenoxim, bromoxynil esters, flumetralin, bromoxynil, flumetralin, butachlor, fluorodifen, butamifos, fluoroglycofen ethyl, butralin, fluoroxypyr esters, butylate, carbetamide, chlomitrofen, chlorpropham, cinmethylin, clethodim, clomazone, clopyralid esters, CMPP esters, cycloate, cycloxydim, desmedipham, dichlorprop esters, flurecol butyl, flurochloralin, haloxyfop, ethoxyethyl, haloxyfop-methyl, ioxynil esters, isopropalin, MCPA esters, mecoprop-P esters, metolachlor, monalide, napropamide, nitrofen, oxadiazon, oxyfluorfen, pendimethalin, phenisopham, phenmedipham, picloram esters, pretilachlor, profluralin, propachlor, propanil, propaquizafop, pyridate, quizalofop-P, triclopyr esters, tridiphane, trifluralin, and the like, and any combination thereof.

Chlorothalonil—The most preferred organic biocide is chlorothalonil, CAS# 1897-45-6, also known as 2,4,5,6-tetrachloro-1,3-dicyanobenzene, chlorothananil, Tetrachloroisophthalonitrile (TCIPN), and 2,4,5,6-tetrachloro-1,3-Benzenedicarbonitrile. Technical chlorothalonil is an odorless, white, crystalline solid melting at about 250° C. Chlorothalonil is commercially available in particles having diameters greater than about 2 microns. Chlorothalonil is variously used in wood preservation to a limited extent, but is also used as a turf and crop fungicide, anti-fouling pigment and mildewcide in coatings. It is substantially insoluble in water (solubility is 0.6–1.2 ppm and is slightly soluble in acetone and xylene. It has low volatility (9.2 mmHg at 170 C). In acid and neutral aqueous preparations, it is relatively stable but has a half life of about 38 days in water at a pH of about 9. It is thermally stable and is resistant to photolysis by ultraviolet radiation. It is also nonvolatile under normal field conditions and is not corrosive. Chlorothalonil is known to be difficult to grind and products are usually supplied as particulates having diameters in the 2–4 micron range because of this.

The process of this invention is capable of producing a series of chlorothalonil products with a procedure that is sufficiently cost effective that the chlorothalonil can be used for foliar agricultural treatments, wood preservatives, and anti-fouling paints, inter alia. These applications are extremely cost sensitive, and the process of this invention can be performed at a cost that is a small fraction of the cost of the raw biocidal material. In various embodiments, the methods of this invention are useful to produce a dispersion of non-agglomerating or interacting particles comprising more than about 20% by weight, typically more than about 50% by weight, and often more than about 80% by weight, of chlorothalonil, with the balance of the particles, if any, typically comprising surface active agents such as stabilizers and dispersants, where the particle size distribution, in various embodiments, can have the following characteristics: A) a volume mean diameter, $d_{50}$, of less than about 1 micron and a $d_{90}$ of less than about 2 microns; B) a volume mean diameter, $d_{50}$, of less than about 0.6 micron and a $d_{90}$ of less than about 1.4 microns, preferably less than about 1 micron; C) a volume mean diameter, $d_{50}$, of less than about 0.4 micron and a $d_{90}$ of less than about 1 micron, preferably less than about 0.7 microns; and/or D) a volume mean diameter, $d_{50}$, between about 0.1 and 0.3 microns and $d_{90}$ that is less than about 3 times the $d_{50}$.

Other organic biocides useful for the process of this invention are those solid biocides listed in U.S. Pat. No. 5,360,783, the disclosure of which is incorporated by reference, including o,o-dimethyl-o-4-methylthio-m-tolyl-phosphorothioate (Baycid), s-4-chlorobenzyldiethylthiocarbamate (Saturn), o-sec-butylphenylmethylcarbamate (BPMC), dimethyl-4,4-(o-phenylene)bis(3-thioallophanate) (Topsin-Methyl), 4,5,6,7-tetrachlorophthalide (Rabcide), o,o-diethyl-o-(2,3-dihydro-3-oxo-2-phenylpyridazin-6-yl)-phosphorothioate (Ofunack) and manganese ethylenebis (dithiocarbamate) (Maneb), where the particle size distribution, in various embodiments, can have the following characteristics: A) a volume mean diameter, $d_{50}$, of less than about 1 micron and a $d_{90}$ of less than about 2 microns; B) a volume mean diameter, $d_{50}$, of less than about 0.6 micron and a $d_{90}$ of less than about 1.4 microns, preferably less than about 1 micron; C) a volume mean diameter, $d_{50}$, of less than about 0.4 micron and a $d_{90}$ of less than about 1 micron, preferably less than about 0.7 microns; and/or D) a volume mean diameter, $d_{50}$, between about 0.1 and 0.3 microns and $d_{90}$ that is less than about 3 times the $d_{50}$. Maneb, for example, is commercially available in particle sizes greater than about 1.4 microns.

In another embodiment, the process of the invention is also useful for preparing a submicron metaldehyde composition. In another embodiment, the process of the invention is also useful for preparing a submicron triphenyltin hydroxide composition. In another embodiment, the process of the invention is also useful for preparing a submicron Mancozeb composition. In another embodiment, the process of the invention is also useful for preparing a submicron Zineb composition. In another embodiment, the process of the invention is also useful for preparing a submicron Ziram composition. In another embodiment, the process of the invention is also useful for preparing a submicron Ferbam composition. In each of these embodiments (and, in fact, with any of the biocides referenced herein), the particle size distribution of the biocide and/or the composition can have the following characteristics: A) a volume mean diameter, $d_{50}$, of less than about 1 micron and a $d_{90}$ of less than about 2 microns; B) a volume mean diameter, $d_{50}$, of less than about 0.6 micron and a $d_{90}$ of less than about 1.4 microns, preferably less than about 1 micron; C) a volume mean diameter, $d_{50}$, of less than about 0.4 micron and a $d_{90}$ of less than about 1 micron, preferably less than about 0.7 microns; and/or D) a volume mean diameter, $d_{50}$, between about 0.1 and 0.3 microns and $d_{90}$ that is less than about 3 times the $d_{50}$.

Generally the processes of this invention produce slurries or suspensions of particulate biocidal material. This material may be dried into a wettable powder, often with the addition of surface active agents and/or fillers, where fillers may include dissolvable buffering agents. The compositions resulting from the processes described herein may alternatively be formulated into fast-dissolving/releasing granules or tablets comprising the submicron organic biocidal material, such that the biocide particles are quickly released to form stable suspensions when the granule contacts water. One example of a biocide composition in tablet form, which rapidly disintegrates and disperses in water, includes, e.g., about 40 parts particulate biocide, about 10 to about 40 parts salts, preferably carbonate and/or bicarbonate salts, about 1 to about 20 parts solid carboxylic acids, about 5 to about 50 parts stabilizers and/or dispersants, and up to about 20 parts starches and/or sugars. Another exemplary dissolvable biocide granule comprises: 1) about 50–75% of a first finely-divided (submicron), essentially water-insoluble biocide, such as is produced by the processes of this invention; 2) optionally about 7–15% of a second particulate biocide, which may be a biocidal inorganic salt; 3) about 2–20% of a stabilizer and/or dispersing agent; 4) about 0.01–10% of a wetting agent; 5) about 0–2% of an antifoaming agent; 6) about 0–10% of a diluent; and optionally 7) about 0–2% of a chelating agent.

Conventional mills used for particulate size reduction in a continuous mode incorporate a means for retaining milling media in the milling zone of the mill, i.e., the milling chamber, while allowing the dispersion or slurry to recirculate through the mill into a stirred holding vessel. Various techniques have been established for retaining media in these mills, including rotating gap separators, screens, sieves, centrifugally-assisted screens, and similar devices to physically restrict passage of media from the mill. The milling process can be a dry process, e.g., a dry milling process, or a wet process, i.e., wet-grinding. In one embodiment, this milling is performed in accordance with the wet milling process of U.S. Pat. No. 5,145,684, using a liquid dispersion medium and a surface modifier described therein. Useful liquid dispersion media include water, aqueous salt solutions, ethanol, butanol, hexane, glycols, and the like. Water, particularly water having added surface active agents, is a preferred medium.

The preferred milling procedure includes wet milling, which is typically done at mill setting between about 1000 rpm and about 4000 rpm, for example between about 2000 rpm and about 3000 rpm. Faster revolutions provide shorter processing times to reach the minimum product particle size.

Generally, the selection of the milling speed, including the speed in a scaled up commercial milling machine, can be readily determined by one of ordinary skill in the art without undue experimentation, given the benefit of this disclosure.

In an alternate procedure, the biocide can be double-milled, e.g., as used to mill chitosan in paragraphs [0070]–[0074] of U.S. Published Patent Application No. 2004/0176477 A1, the disclosure of which is incorporated by reference herein. In one such embodiment, for example, the milling media in the first milling step can have a diameter of about 0.5 to 1 mm, preferably 0.5 to 0.8 mm, while the milling media in the second milling step can have a diameter of about 0.1–0.4 mm, preferably about 0.3 mm.

The milling temperature of the organic biocide can be at least about 40° C. below, preferably at least about 100° C. below the glass transition temperature (or the softening temperature, if there is no glass transition temperature, or the melting temperature, if the biocide is inorganic). Preferably, the milling takes place at a process temperature of about ambient temperature to about 40° C. To maintain an ambient milling temperature, generally active cooling is required, and the cost of active cooling generally exceeds the benefit obtained.

The milling media, also called grinding media or milling beads, is central to this invention. The use of this medium is novel and achieves an unexpected reduction in particle size and in particle size distribution that was not anticipated looking at prior art results of milling, and that allows a variety of new uses for the biocide products and of significant reductions in dosage compared to prior art chlorothalonil formulations. The selection of milling media is therefore expressly not a routine optimization. The use of this media allows an average particle size and a narrow particle size distribution that had previously not been obtainable or foreseeable in the art.

The milling media advantageously comprises or consists essentially of a zirconium-based milling beads. The preferred media is zirconia (density ~6 g/cm$^3$), which includes preferred variants such as yttria stabilized tetragonal zirconium oxide, magnesia stabilized zirconium oxide, and cerium doped zirconium oxide. For some biocides, zirconium silicate (density ~3.8 g/cm$^3$) is useful. However, for several biocides such as chlorothalanil, zirconium silicate will not achieve the required action needed to obtain the narrow sub-micron range of particle sizes in several preferred embodiments of this invention.

In an alternate embodiment, at least a portion of the milling media comprises or consists essentially of metallic material, e.g., steel.

The milling medium is a material having a density greater than about 3.5, preferably at least about 3.8, more preferably greater than about 5.5, for example at least about 6 g/cm$^3$.

We believe that density and particle size are the two most important parameters in the milling media. Preferably the milling media comprises or consists essentially of particles, having a size (diameter) between about 0.1 mm and about 0.8 mm, preferably between about 0.3 mm and about 0.7 mm, for example between about 0.4 mm and 0.6 mm. Also preferably, the milling media can have a density greater than about 3.8 g/cm$^3$, preferably greater than about 5 g/cm$^3$, more preferably greater than about 6 g/cm$^3$.

The zirconium-based milling media useful in the present invention can comprise or consist essentially of particles having a diameter (as the term is used in the art) between about 0.1 mm and about 0.8 mm, preferably between about 0.3 mm and about 0.7 mm, for example between about 0.4 mm and 0.6 mm. The media need not be of one composition or size. Preferably at least about 10%, preferably about 25%, alternately at least about 30%, for example between about 50% and about 99%, of the media has a mean diameter of between about 0.1 mm to about 0.8 mm, preferably between about 0.3 mm and about 0.6 mm, or alternatively between about 0.3 mm and about 0.5 mm. The remaining media (not within the specified particle size) can be larger or smaller, but, in preferred embodiments, the media not within the specified size is larger than the media in the specified size, for example at least a portion of the milling media not within the preferred size range(s) has a diameter between about 1.5 and about 4 times, for example between about 1.9 and about 3 times, the diameter of the preferred media. A preferred media is 0.5 mm zirconia, or a mixture of 0.5 mm zirconia and 1–2 mm zirconia, where at least about 25% by weight of the media is 0.5 mm zirconia. The remaining media need not comprise zirconium, but advantageously will have a density greater than 3.5 g/cc. Using media comprising a zircinia portion and a steel portion can be advantageous.

In an alternate embodiment, the metal, e.g., steel milling media useful in the present invention can comprise or consist essentially of particles having a diameter (as the term is used in the art) between about 0.1 mm and about 0.8 mm, preferably between about 0.3 mm and about 0.7 mm, for example between about 0.4 mm and 0.6 mm. The media need not be of one composition or size. Preferably at least about 10%, preferably about 25%, alternately at least about 30%, for example between about 50% and about 99%, of the media has a mean diameter of between about 0.1 mm to about 0.8 mm, preferably between about 0.3 mm and about 0.6 mm, or alternatively between about 0.3 mm and about 0.5 mm. The remaining media (not within the specified particle size) can be larger or smaller, but, in preferred embodiments, the media not within the specified size is larger than the media in the specified size, for example at least a portion of the milling media not within the preferred size range(s) has a diameter between about 1.5 and about 4 times, for example between about 1.9 and about 3 times, the diameter of the preferred media. The remaining media need not comprise steel, but advantageously will have a density greater than 3.5 g/cc.

Advantageously, the average diameter of the milling media is preferably about 0.4 mm to about 0.6 mm, and more preferably about 0.5 mm, and is preferably zirconia. If other media or sizes are present, beneficially at least about 25%, preferably at least about 50%, by weight of the milling media has an average particulate diameter of about 0.4 mm to about 0.6 mm, and more preferably about 0.5 mm. Such media will provide the desired submicron and narrow particle size distribution described herein. Generally, the use of milling media below about 0.1 mm diameter is discouraged, unless it is present with the recited amount of media in the preferred size range. Generally, the milling media within the specified size ranges of about 0.1 mm to about 0.8 mm, for example form about 0.1 mm to about 0.7 mm or from about 0.1 mm to 0.6 mm, or alternatively from about 0.3 mm to about 0.6 mm or from about 0.4 mm to about 0.5 mm, comprises or consists essentially of a zirconium-containing compound, preferably zirconia.

Advantageously, the milling media loading can be between about 40% and about 80% of the mill volume.

Advantageously, the organic biocide can be milled for a time between about 10 minutes and about 8 hours, preferably between about 10 minutes and about 240 minutes, for example between about 15 minutes and about 150 minutes. Again, the upper limit in time is significantly less important than the lower limit, as the change in particle size distribution per hour of milling becomes exceedingly small as the milling time increases.

Ostwald ripening can occur whenever a component of the disperse phase is capable of being transported through the continuous phase from one particle to another. The usual mechanism for such transport is by dissolution of the transportable material in the continuous phase, which can occur even if the solubility of the material is low. Other transport mechanisms, however, are possible. For example, even materials having a very low water solubility indeed, which might not be expected to display Ostwald ripening, can do so, when certain surfactants are used in the preparation and stabilization of the emulsion. Such a phenomenon is believed to be due to transport of the water insoluble materials through the aqueous phase by dissolution in surfactant micelles. Various compounds to alleviate this problem are described, for example, in U.S. Pat. No. 6,074,986, the disclosure of which is incorporated by reference. On the other hand, some particles can get smaller with time.

Aqueous dispersing agents for such dispersed solids are well known to those skilled in the art and include, but are not limited to, nonionic surfactants such as ethylene oxide/propylene oxide block copolymers, polyvinyl alcohol/polyvinyl acetate copolymers, polymeric nonionic surfactants such as the acrylic graft copolymers; anionic surfactants such as polyacrylates, lignosulfonates, polystyrene sulfonates, maleic anhydride-methyl vinyl ether copolymers, naphthalene sulfonic acid formaldehyde condensates, phosphate ester surfactants such as a tristyrenated phenol ethoxylate phosphate ester, maleic anhydride-diisobutylene copolymers, anionically modified polyvinyl alcohol/polyvinylacetate copolymers, and ether sulfate surfactants derived from the corresponding alkoxylated nonionic surfactants; cationic surfactants; zwitterionic surfactants; and the like.

The milling of the organic biocides is advantageously performed in the presence of an aqueous medium containing surfactants and/or dispersants, such as those known in the art. Use of other media, including for example polar organic solvents such as alcohols, generally does not offer added advantage sufficient to outweigh the cost and associated hazards of milling with solvents. Because it is now possible to achieve a smaller particle size and a narrower particle size distribution using the present invention than was previously known in the art, the number and amount of stabilizers and/or dispersants are less critical. As used herein, the term "surface active agent" includes both singlular and plural forms and encompasses generally both stabilizers and dispersants. The surface active agent may be anionic, cationic, zwitterionic, or nonionic, or a combination thereof. Generally, higher concentrations of surface active agents present during milling result in a smaller particle size.

However, because we have surprisingly found a milling media and conditions where very small particles and a narrow particle size distribution are obtainable, we can use less/lower amounts of stabilizers and/or dispersants than would otherwise be used. For example, advantageously the total weight of surface active agents in the present invention can be less than about 1.5 times the weight of the particulate organic biocide, preferably less than about the weight of the particulate organic biocide. A stabilizing amount of the surface active agent can be used, generally not less than about 2%, and typically not more than about 60% by weight, based on the weight of the particulate organic biocide. Other adjuvants, such as: fillers including biocidal fillers such as zinc oxide and non-biocidal fillers such as silica; stabilizer/dispersants such as a poly (oxypropylene) block copolymer with poly (oxyethylene), commercially available from BASF, PROXEL GXL (1,2-benzisothiazolin-3-one, commercially available from ICI, and/or PVP K-30 poly(vinyl pyrrolidone), commercially available from BAS; typical viscosity modifiers/stabilizers such as xanthan gum commercially available from Kelco); typical anti-foaming agents such as Antifoam FG-10, a silicon emulsion commercially available from Dow Corning; antifreeze such as propylene glycol; chelators such as EDTA, HEDP, and the like, can be added to the water before or during milling. Milling is best done in a wet mill or high speed media mill.

Examples of suitable classes of surface active agents include, but are not limited to, anionics such as alkali metal fatty acid salts, including alkali metal oleates and stearates; alkali metal lauryl sulfates; alkali metal salts of diisooctyl sulfosuccinate; alkyl aryl sulfates or sulfonates, lignosulfonates, alkali metal alkylbenzene sulfonates such as dodecylbenzene sulfonate, alkali metal soaps, oil-soluble (e.g., calcium, ammonium, etc.) salts of alkyl aryl sulfonic acids, oil soluble salts of sulfated polyglycol ethers, salts of the ethers of sulfosuccinic acid, and half esters thereof with nonionic surfactants and appropriate salts of phosphated polyglycol ethers; cationics such as long chain alkyl quaternary ammonium surfactants including cetyl trimethyl ammonium bromide, as well as fatty amines; nonionics such as ethoxylated derivatives of fatty alcohols, alkyl phenols, polyalkylene glycol ethers and condensation products of alkyl phenols, amines, fatty acids, fatty esters, mono-, di-, or triglycerides, various block copolymeric surfactants derived from alkylene oxides such as ethylene oxide/propylene oxide (e.g., PLURONIC™, which is a class of nonionic PEO-PPO co-polymer surfactant commercially available from BASF), aliphatic amines or fatty acids with ethylene oxides and/or propylene oxides such as the ethoxylated alkyl phenols or ethoxylated aryl or polyaryl phenols, carboxylic esters solubilized with a polyol or polyvinyl alcohol/polyvinyl acetate copolymers, polyvinyl alcohol, polyvinyl pyrrolidinones (including those sold under the tradenames AGRIMER™ and GANEX™), cellulose derivatives such as hydroxymethyl cellulose (including those commercially available from Dow Chemical Company as METHOCEL™), and acrylic acid graft copolymers; zwitterionics; and the like; and mixtures, reaction products, and/or copolymers thereof.

Additionally or alternatively, the surface active agent may include, but is not limited to, low molecular weight sodium lauryl sulfates, calcium dodecyl benzene sulfonates, tristyryl ethoxylated phosphoric acid or salts, methyl vinyl ether-maleic acid half-ester (at least partially neutralized), beeswax, water soluble polyacrylates with at least 10% acrylic acids/salts, or the like, or a combination thereof.

Additionally or alternatively, the surface active agent may include, but is not limited to, alkyl grafted PVP copolymers commercially available as GANEX™ and/or the AGRIMER™ AL or WP series, PVP-vinyl acetate copolymers commercially available as the AGRIMER™ VA series, lignin sulfonate commercially available as REAX 85A (e.g., with a molecular weight of about 10,000), tristyryl phenyl ethoxylated phosphoric acid/salt commercially available as SOPROPHOR™ 3D33, GEROPON™ SS 075, calcium dodecylbenzene sulfonate commercially available as NINATE™ 401 A, IGEPAL™ CO 630, other oligomeric/polymeric sulfonated surfactants such as Polyfon H (molecular weight ~4300, sulfonation index ~0.7, salt content ~4%), Polyfon T (molecular weight ~2900, sulfonation index ~2.0, salt content ~8.6%), Polyfon O (molecular weight ~2400, sulfonation index ~1.2, salt content ~5%), Polyfon F (molecular weight ~2900, sulfonation index ~3.3, salt content ~12.7%), Reax 88B (molecular weight ~3100, sulfonation index ~2.9, salt content ~8.6%), Reax 100 M (molecular weight ~2000, sulfonation index ~3.4, salt content ~6.5%), and Reax 825 E (molecular weight ~3700, sulfonation index ~3.4, salt content ~5.4%), and the like.

Other notable surface active agents can include nonionic polyalkylene glycol alkyd compounds prepared by reaction of polyalkylene glycols and/or polyols with (poly)carboxylic acids or anhydrides; A-B-A block-type surfactants such as those produced from the esterification of poly(12-hydroxystearic acid) with polyalkylene glycols; high molecular weight esters of natural vegetable oils such as the alkyl esters of oleic acid and polyesters of polyfunctional alcohols; a high molecular weight (MW>2000) salt of a naphthalene sulfonic acid formaldehyde condensate, such as GALORYL™ DT 120L available from Nufarm; MORWET EFW™ available from Akzo Nobel; various Agrimer™ dispersants available from International Specialties Inc.; and a nonionic PEO-PPO-PEO triblock co-polymer surfactant commercially available as PLURONIC™ from BASF.

Other examples of commercially available surface active agents include Atlox 4991 and 4913 surfactants (Uniqema), Morwet D425 surfactant (Witco), Pluronic P105 surfactant (BASF), Iconol TDA-6 surfactant (BASF), Kraftsperse 25M surfactant (Westvaco), Nipol 2782 surfactant (Stepan), Soprophor FL surfactant (Rhone-Poulenc), Empicol LX 28 surfactant (Albright & Wilson), Pluronic F108 (BASF).

In one embodiment, exemplary suitable stabilizing components include polymers or oligomers having a molecular weight from about 250 to about $10^6$, preferably from about 400 to about $10^5$, more preferably from about 400 to about $10^4$, and can include, for example, homopolymers or co-polymers described in "Polymer Handbook," 3rd Edition, edited by J. Brandrup and E. H. Immergut.

In another embodiment, exemplary suitable stabilizing components include polyolefins such as polyallene, polybutadiene, polyisoprene, poly(substituted butadienes) such as poly(2-t-butyl-1,3-butadiene), poly(2-chlorobutadiene), poly(2-chloromethyl butadiene), polyphenylacetylene, polyethylene, chlorinated polyethylene, polypropylene, polybutene, polyisobutene, polybutylene oxides, copolymers of polybutylene oxides with propylene oxide or ethylene oxide, polycyclopentylethylene, polycyclolhexylethylene, polyacrylates including polyalkylacrylates and polyarylacrylates, polymethacrylates including polyalkylmethacrylates and polyarylmethacrylates, polydisubstituted esters such as poly(di-n-butylitaconate), poly(amylfumarate), polyvinylethers such as poly(butoxyethylene) and poly(benzyloxyethylene), poly(methyl isopropenyl ketone), polyvinyl chloride, polyvinyl acetate, polyvinyl carboxylate esters such as polyvinyl propionate, polyvinyl butyrate, polyvinyl caprylate, polyvinyl laurate, polyvinyl stearate, polyvinyl benzoate, polystyrene, poly-t-butyl styrene, poly (substituted styrene), poly(biphenyl ethylene), poly(1,3-cyclohexadiene), polycyclopentadiene, polyoxypropylene, polyoxytetramethylene, polycarbonates such as poly(oxycarbonyloxyhexamethylene), polysiloxanes, in particular, polydimethyl cyclosiloxanes and organo-soluble substituted polydimethyl siloxanes such as alkyl, alkoxy, or ester substituted polydimethylsiloxanes, liquid polysulfides, natural rubber and hydrochlorinated rubber, ethyi-, butyl- and benzyl-celluloses, cellulose esters such as cellulose tributyrate, cellulose tricaprylate, and cellulose tristearate, natural resins such as colophony, copal, and shellac, and the like, and combinations or copolymers thereof.

In still another embodiment, exemplary suitable stabilizing components include co-polymers of styrene, alkyl styrenes, isoprene, butenes, butadiene, acrylonitrile, alkyl acrylates, alkyl methacrylates, vinyl chloride, vinylidene chloride, vinyl esters of lower carboxylic acids, and α,β-ethylenically unsaturated carboxylic acids and esters thereof, including co-polymers containing three or more different monomer species therein, as well as combinations and copolymers thereof.

In yet another embodiment, exemplary suitable stabilizing components include polystyrenes, polybutenes, for example polyisobutenes, polybutadienes, polypropylene glycol, methyl oleate, polyalkyl(meth)acrylate e.g. polyisobutylacrylate or polyoctadecylmethacrylate, polyvinylesters e.g. polyvinylstearate, polystyrene/ethyl hexylacrylate copolymer, and polyvinylchloride, polydimethyl cyclosiloxanes, organic soluble substituted polydimethyl siloxanes such as alkyl, alkoxy or ester substituted polydimethylsiloxanes, and plybutylene oxides or copolymers of polybutylene oxides with propylene and/or ethylene oxide.

In one embodiment, the surface active agent can be adsorbed onto the surface of the biocide particle, e.g., in accordance with U.S. Pat. No. 5,145,684.

Additionally, other additives may be included in the biocidal compositions according to the invention for imparting particular advantages or to elicit particular properties. These additives are generally known in the solution, emulsion, and/or slurry arts, and can include, e.g., anti-freeze agents such as glycols (for instance, ethylene and/or propylene glycol), inter alia.

The composition preferably comprises between about 0.05% and about 50% by weight of the particulate organic biocide, e.g., chlorothalonil, or a mixture of two or more particulate biocides where one particulate biocide is the organic particulate biocide and the other particulate biocide is selected from other particulate organic biocides, particulate organometallic biocides (e.g., Maneb), slightly soluble inorganic biocides (e.g., copper hydroxide), or a combination thereof.

One of the advantages of the stable aqueous dispersion of the present invention is that it provides a means to prepare one-part formulations of different biocides which are not only compatible with each other, but incompatible or unstable in each other's presence as well. For example, it may be desirable to combine a certain pesticide with a certain herbicide for a particular application but for the fact that the two biocides (in solution, for example) react with each other faster than they can be applied to the desired site. However, in a stable aqueous dispersion of particulate biocides, these different and incompatible biocides can co-exist, at least temporarily, since they are shielded from each other from reacting rapidly, so that an end user can mix the incompatible pesticides together and apply them to a site before their efficacy is significantly diminished.

The particulate organic biocide is, in many embodiments, combined with one or more other organic biocides and/or particulate sparingly soluble biocidal inorganic salts. These inorganic biocidal salts can be milled, for example, using the same procedures and importantly the same milling media described for the organic pesticides. For instance, particulate copper(I) oxide is useful and is readily milled by the processes of this invention.

Preferred inorganic copper salts include copper hydroxides; copper carbonates; basic (or "alkaline") copper carbonates; basic copper sulfates including particularly tribasic copper sulfate; basic copper nitrates; copper oxychlorides (basic copper chlorides); copper borates; basic copper borates; copper silicate; basic copper phosphate; and mixtures thereof. The particulate copper salts can have a substantial amount of one or more of magnesium, zinc, or both, e.g., between about 6 and about 20 parts of magnesium per 100 parts of copper, for example between about 9 and about 15 parts of magnesium per 100 parts of copper, wherein these cations are either dispersed within, or constitute a separate phase within, a particulate. In preferred embodiments of the invention, at least some particulates comprise copper hydroxide, basic copper carbonate, or both.

Preferred inorganic zinc salts and compounds include the zinc complements of the aforementioned copper salts, and expressly includes zinc oxide; the synergystic use of zinc oxide and chlorothalonil for potatoes is described in U.S. Pat. No. 5,667,795, the disclosure of which is incorporated herein by reference. This patent teaches that 2–4 micron diameter chlorothalonil particles were useful with 1–4 micron diameter zinc oxide particles. However, we believe the claimed range in this publication reflected what the inventors could manufacture. In contrast, the preferred particle size range has a chlorothalonil $d_{50}$ less than about 1.4 microns, for example not more than about 0.9 microns or less than about 0.5 microns, alternately from about 0.1 microns to about 0.35 microns, and preferably has a $d_{80}$ less than about 0.5 microns, while the zinc oxide is useful with a $d_{50}$ less than about 1.5 microns, for example less than about 1 micron, e.g., between about 0.3 and about 0.7 microns. Other useful zinc salts include zinc hydroxide, zinc carbonate, zinc oxychloride, zinc fluoroborate, zinc borate, zinc fluoride, and mixtures thereof.

Additionally or alternately, selected finely ground crystalline iron oxides and hydroxides (excluding gel-like materials such as Goethite) can provide UV protective activity to wood and, like the copper and zinc salts described above, can be readily milled to form injectable slurries using processes of this invention, can be readily co-mingled with the particulate organic biocide, and can be injected into the wood or used in paint. Indeed, the media of this invention can mill certain iron oxides to a d50 below 0.1 microns. This iron salt can also be used as a pigment, to help disguise the color of other components injected. Selected sparingly soluble nickel salts and finely ground nickel oxide can provide biocidal activity to wood, and like the copper and zinc salts described above, can be readily milled to injectable slurries using processes of this invention, can be readily co-mingled with the particulate organic biocide, and can be injected into wood or used in paint. Selected sparingly soluble tin salts and finely ground tin oxide can provide biocidal activity to wood and, like the copper and zinc salts described above, can be readily milled to injectable slurries using processes of this invention, can be readily co-mingled with the particulate organic biocide, and can be injected into wood or used in paint.

Selected copper salts of an unsaturated dibasic acid, such as fumaric acid, maleic acid, mesaconic acid, terephthalic acid, isophthalic acid, and the like, as well as other compounds described in U.S. Pat. No. 4,075,326, can be formed into solids and milled according to the processes of the current invention. Other moieties, including particularly sulfonate moieties, can be substituted for one or both of the carboxylate moieties in the dibasic acids described above, and the resulting copper salt may again be sparingly soluble and thus grindable and usable in the methods according to the invention. Further, copper salts of organic acids having two carboxylate moieties separated by not one carbon atom but by two carbon atoms, e.g., copper succinate or the like, can be ground and treated like other organic copper salts.

One or more liquid organic biocides can be coated onto the particulate organic biocide, or onto the inorganic particulate biocide, if available, or both. An emulsion having dispersed liquid biocides in a small amount of solvent can be added to a composition containing the to-be-milled biocide before or during milling, for example, and the solvent can be removed by evaporation or vacuum distillation to leave the non-volatile liquid organic biocide, for example a triazole such as tebuconazole, coated onto the particulates. In addition to combining synergistic combinations of biocides, this process could help more evenly distribute the liquid biocide, which is often present in very small quantities.

Foliar Applications—Generally, the size of the particles for use in foliar applications will depend on the required duration of treatment as well as on the weathering-resistance of each biocide. For biocides that are substantially insoluble, like chlorothalonil, usually only the resistance to weathering is important. A small particle size coupled with a narrow particle size distribution will allow a substantial reduction in the required dosage. This invention provides both a method of manufacture and the product of this method, that is, a method of producing a chlorothalonil product where the $d_{50}$ is below 1 micron, preferably below 0.7 microns, and for certain applications, below 0.4 microns, for example between about 0.1 microns and about 0.3 microns.

While generally the maximum particle sizes are specified, the minimum particle sizes are also central to the use of these particles in foliar applications. Generally, a particle, particularly a chlorothalonil particle, particle size $d_{50}$ should be greater than about 0.05 microns, for example greater than about 0.1 microns, to ensure the particles have commercially desirable duration of treatment when exposed to the environment. In one preferred embodiment the particles have a $d_{50}$ of about 0.1 microns or greater, and a $d_{90}$ of greater than on third the $d_{50}$.

Another embodiment of this invention is providing a method of producing a metaldehyde product where the $d_{50}$ is below 1 micron, preferably below 0.7 microns, and for certain applications, below 0.4 microns, for example between about 0.1 microns and about 0.3 microns. Another embodiment of this invention is providing a method of producing a zineb product where the $d_{50}$ is below 1 micron, preferably below 0.7 microns, and for certain applications, below 0.4 microns, for example between about 0.1 microns and about 0.3 microns. Another embodiment of this invention is providing a method of producing a Ziram product where the $d_{50}$ is below 1 micron, preferably below 0.7 microns, and for certain applications, below 0.4 microns, for example between about 0.1 microns and about 0.3 microns. Another embodiment of this invention is providing a method of producing a Ferbam product where the $d_{50}$ is below 1 micron, preferably below 0.7 microns, and for certain applications, below 0.4 microns, for example between about 0.1 microns and about 0.3 microns. Another embodiment of this invention is providing a method of producing a maneb product, a Mancozeb product, and a Maneb/Mancozeb product where the $d_{50}$ is below 1 micron, preferably below 0.7 microns, and for certain applications, below 0.4 microns, for example between about 0.1 microns and about 0.3 microns. Another embodiment of this invention is providing a method of producing a TPTH product where the $d_{50}$ is below 1 micron, preferably below 0.7 microns, and for certain applications, below 0.4 microns, for example between about 0.1 microns and about 0.3 microns.

For foliar applications, the advantageously narrow particle size distribution is also provided by the method of producing a each of the above products, where the $d_{90}$ is less than about 4 times the $d_{50}$, preferably less than three times the $d_{50}$; where the $d_{90}$ is advantageously greater than about ¼th the $d_{50}$, preferably greater than about ⅓rd the $d_{50}$. Indeed, in the example the $d_{95}$ was of the milled chlorothalonil was within a factor of about 2 of the $d_{50}$.

One aspect of the invention relates to stable aqueous dispersions of the organic biocide, e.g., chlorothalonil, that can be prepared by wet milling an aqueous dispersion of the biocide in the presence of grinding media and a surface active agent, for use in foliar-type agricultural treatments, for example. For foliar treatment, the composition is generally combined with water to provide a stable suspension having the desired concentration, and this stable suspension is then broadcast onto the crops, as is known in the art.

In foliar applications, a smaller size particle is generally more persistent than a larger size particle against degenerative/deactivating forces such as rain. The preparation can be carried out in such a manner so as to produce a dispersion of non-agglomerating or non-interacting particles having a volume median diameter, $d_{50}$, of less than about 1 micron and a $d_{90}$ of less than about 2 microns. In preferred embodiments, the preparation is carried out in such a manner so as to produce a dispersion of non-agglomerating or non-interacting particles having a volume median diameter, $d_{50}$, of less than about 0.6 micron and a $d_{90}$ of less than about 1.4 microns, preferably less than about 1 micron. In other preferred embodiments, the preparation is carried out in such a manner so as to produce a dispersion of non-agglomerating or non-interacting particles having a volume median diameter, $d_{50}$, of less than about 0.4 micron and a $d_{90}$ of less than about 1 micron, preferably less than about 0.7 microns. For example, the method according to the invention may advantageously produce a slurry where $d_{50}$ is between about 0.1 and about 0.3 microns and where $d_{90}$ is less than about 3 times $d_{50}$.

Anti-Fouling Coating Applications—For anti-fouling paints and coatings, if there are combinations of particulate biocides, the size of the particulates should be within a factor of about 5 of the size of the remaining particulates, though it is recognized that biocides with higher solubility may require larger particles to have the desired duration of effectiveness. One aspect of the invention relates to stable aqueous dispersions of the organic biocide, e.g., chlorothalonil, that can be prepared by wet milling an aqueous dispersion containing the biocide in the presence of grinding media and a surface active agent, for use in anti-fouling paints and coatings, for example.

It is known to use 0.5 mm zirconia as a milling media for certain pigments to be used in paints. U.S. Published Patent Application No. 2003/0127023 A1 teaches that pigments having improved colouristic properties and process for their preparation, and describes examples where compositions containing pigments and additives are milled with 0.5 mm diameter zirconia milling media. In this publication, Igaphor™ DPP Red B-CF (mean particle size about 50 nm, available from Ciba Specialty Chemicals Inc) was admixed in a vessel with 8 mg Solsperse™ S22000 (Zeneca); 32 mg Solsperse™ S24000 (Zeneca); 200 mg of a copolymer of aromatic methacrylates and methacrylic acid (MW from 30,000 to 60,000); 1.76 g of (1-methoxy-2-propyl)-acetate; and 5 g zirconia beads of diameter 0.5 mm. The vessel was sealed with an inner cup placed in an operating paint conditioner for 3 hours, in order to yield a dispersion. The milled pigments forming the ingredients in this patent were all less than 0.2 microns in average diameter before milling, and most examples contained pigments with average particle size less than 0.1 microns before milling. This illustrates the advantage of this invention. Generally, it is known that pigments in paints form a more impermeable layer if the particle size of the pigments is reduced. However, this has not been applied to the biocides—until now, there was no economical and reliable method of obtaining chlorothalonil, for example, at such a small particle size. Now, our method allows a variety of biocidal agents approved for use in anti-fouling paints and coatings to be reliably milled to provide both the desired submicron $d_{50}$ but also to provide the desired narrow particle size distribution, exemplified by $d_{90}$ (and preferably $d_{95}$) being less than about twice the $d_{50}$.

Commonly used biocides in marine applications includes copper(I) oxide, copper thiocyanate, Cu powder, zinc oxide, chromium trioxide, Irgarol™ 1051, zinc pyrithione, dichlofluanid, TCMBT (2-(thiocyanomethylthio) benzothiazole, a liquid biocide), chlorothalonil, 2,3,5,6-tetrachloro-4-sulfuronyl pyridine, SeaNine 211 (4,5-dicholo-2-n-octyl-4-isothiazolin-3-one), ziram (zinc dimethyldithiocarbamate or bis(dimethylcarbamodithioato-S,S')zinc), zineb, folpet, and the like. Generally, the particles are held in place by the paint or coating matrix. The sizes of the particulate biocides are therefore primarily a function of the anticipated duration of the treatment and the biocide dissolution rate, and are also a function of the desired particle size for the paint or coating. Finer particles make smoother and less permeable coatings. The copper oxide, zinc oxide, and the chlorothalonil are particularly suited for milling into submicron-sized particles using the procedures described herein, having, e.g., $d_{50}$ from about 0.1 to about 0.9 microns, and, e.g., a $d_{90}$ less than three times, preferably less than two times, the $d_{50}$ value. For instance, one example would be a composition with a $d_{50}$ of about 0.2 microns and a $d_{50}$ of about 0.4 microns or less. Such small particles, when combined with adequate particle size distribution control, would provide greater coverage, less permeability, and more gloss than was previously obtainable with formulations using larger particulates having a wider size distribution.

The preparation is carried out in such a manner so as to produce a dispersion of non-agglomerating or non-interacting particles having a volume median diameter, $d_{50}$, of less than about 1 micron and a $d_{90}$ of less than about 2 microns. In preferred embodiments, the preparation is carried out in such a manner so as to produce a dispersion of non-agglomerating or non-interacting particles having a volume median diameter, $d_{50}$, of less than about 0.6 microns and a $d_{90}$ of less than about 1.4 microns, preferably less than about 1 micron. In other preferred embodiments, the preparation is carried out in such a manner so as to produce a dispersion of non-agglomerating or non-interacting particles having a volume median diameter, $d_{50}$, of less than about 0.4 micron and a $d_{90}$ of less than about 1 micron, preferably less than about 0.7 microns. For example, the method according to the invention may advantageously produce a slurry where $d_{50}$ is between about 0.1 and about 0.3 microns and where $d_{90}$ is less than about 3 times $d_{50}$.

Injectable Wood Preservative Applications—For wood treatments, the overriding consideration is that the particles of each biocide, and of the combined biocides, be injectable into the wood matrix.

One aspect of the invention relates to stable aqueous dispersions of the organic biocide, e.g., chlorothalonil, that can be prepared by wet milling an aqueous dispersion of the biocide in the presence of grinding media and a surface active agent, for use as an injectable wood preservative, for example. The injectable particulate organic biocide can, for example, comprise chlorothalonil, metaldehyde, manganese ethylenebis(dithiocarbamate) (Maneb), salts thereof, or mixtures thereof.

Another aspect of the invention relates to wood or a wood product comprising a milled biocide according to the invention and, optionally, one or more additional materials having a preservative function, injected into a piece of wood. The concurrent use of other organic biocides, inorganic biocidal sparingly soluble salts and/or oxides, and liquid organic biocides coated onto the particulate biocides can be particularly useful for treating wood, where combinations of biocides are commonly used.

The requirements of injectability for substantially round/spherical particles (e.g., in which the diameter is one direction is within a factor of two of the diameter measured in an orthogonal direction) include, but are not limited to, the following: where $d_{98}$ is not more than about 0.5 microns, preferably not more than about 0.3 microns, for example not more than about 0.2 microns; and/or where the $d_{96}$, preferably the $d_{99}$, is less than about 1.5 microns, preferably less than about 1 micron, for example less than about 0.7 microns. The preparation is carried out in such a manner so as to produce a dispersion of non-agglomerating or non-interacting particles that meet the above requirements, and further having a volume median diameter, $d_{50}$, of less than about 0.4 microns and preferably a $d_{96}$ of less than about 0.7 microns. Different wood materials require different particle sizes, but the above ranges are generally sufficient for Southern Pine wood.

In preferred embodiments, the preparation is carried out in such a manner so as to produce a dispersion of non-agglomerating or non-interacting particles having a volume median diameter, $d_{50}$, of less than about 0.35 microns and a $d_{95}$ of less than about 0.7 microns, preferably less than about 0.5 microns. In other preferred embodiments, the preparation is carried out in such a manner so as to produce a dispersion of non-agglomerating or non-interacting particles having a volume median diameter, $d_{50}$, of less than about 0.3 microns and a $d_{95}$ of less than about 0.6 microns, preferably less than about 0.5 microns. For example, the method according to the invention may advantageously produce a slurry where $d_{50}$ is between about 0.1 and about 0.3 microns and where $d_{90}$ is less than about 3 times $d_{50}$. In one preferred embodiment, at least 80% by weight of the organic biocide particulates have a size/diameter between about 0.05 microns and about 0.4 microns.

The requirements of injectability for substantially round/spherical, rigid particles (e.g., in which the diameter is one direction is within a factor of two of the diameter measured in an orthogonal direction) generally include, inter alia: 1) that substantially all the particles, e.g., greater than about 98% by weight, have a particle size with diameter not more than about 0.5 microns, for example not more than about 0.3 microns or not more than about 0.2 microns; and 2) that substantially no particles (e.g., less than about 0.5% by weight) have a diameter greater than about 1.5 microns, or an average diameter greater than about 1 micron, for example. We found, from experiments with sparingly soluble salts ground in using the same procedures as specified herein, that such milling provided a product that was readily injectable into wood. We believe the first criterion primarily addresses the phenomena of bridging and subsequent plugging of pore throats, and the second criterion addresses the phenomena of forming a plug, or filter cake. Once a pore throat is partially plugged, complete plugging and undesired buildup generally quickly ensues.

In one embodiment, the size distribution of the injectable particles requires that the vast majority of particles (for example at least about 95% by weight, preferably at least about 99% by weight, more preferably at least about 99.5% by weight) be of an average diameter less than about 1 micron. On the other hand, the minimum size of the particles is less important, since particles in the wood will be partially protected by the environment, e.g., from the sun. The minimum d50 can be between about 0.01 and 0.1 microns, but a preferred minimum $d_{50}$ is 0.5 microns or 0.1 microns. A distribution of sizes, insofar as the distribution is injectable into wood, is beneficial, as it provides a fraction of biocidal particles having a useful lifetime greater than that of the average particle size. This is true, of course, only if the core of the particulate is formed only of the substantially insoluble biocidal material. Inclusions of surfactants and such within the biocidal material, as opposed to on the exteriors of the biocidal particles, can accelerate disintegration of the injected particle.

Milling is advantageously performed with the dispersants and surface active agents. The slurry for injection into wood may comprise soluble copper such as aqueous copper monoethanolamine carbonate, or finely ground sparingly soluble copper salts, preferably copper hydroxide or a basic copper salt, e.g., pregferably basic copper carbonate but also optionally including basic copper sulfate, basic copper phosphate, basic copper nitrate, and the like. Advantageously the inorganic particulates such as the sparingly soluble copper salts have approximately the same $d_{50}$ as the ground organic biocide, e.g., within a factor of two or three, and has similar limitations on the particle size distribution. Other components can be added, including other milled components—zinc oxide provides complementary biocidal activity, copper (I) oxide provides very low levels of biocidal activity but is extremely long lasting, and various iron oxide pigments can provide protection of wood very near the surface from UV radiation. Any combination of these can be formed into a slurry which is readily injected into wood using standard industry procedures, and is retained at levels generally well over 95%.

Its generally not advantageous to mill various components at the same time—each component should be individually milled to its required specifications, and then the slurry can be prepared to specification by mixing components. One exception may be where the organic biocide being milled is too plastic to obtain the desired particle size, in which case it may be advantageous to add a quantity of small particulate, millable material with high porosity, such as alumina. Milling certain biocides in combination with submicron alumina and with the required dispersants may allow particularly resistant biocides to be milled into a size amenable for injection into wood.

Other aspects of the present invention include methods for preparing the ground biocide particulates according to the invention, methods of formulating injectable wood treatment compositions that comprise ground biocide particulates, methods of transporting the injectable wood treatments, methods of mixing and injecting the ground biocide particulate composition according to the invention into wood and/or wood products, and also the wood and wood products themselves treated with the ground biocide particulate compositions according to the invention.

Injectability can and often does require that the particulates be substantially free of the size and morphology that will tend to accumulate and form a plug or filter cake, generally on or near the surface of the wood, that results in undesirable accumulations on wood in one or more outer portions of the wood and thus a deficiency in an inner portion of the wood. Injectability is generally a function of the wood itself, as well as the particle size, particle morphology, particle concentration, and the particle size distribution. We recognize that a competitor may spike a composition with a small number of very large particles, in a quantity where the very large particles are not injected but are also not present in an amount which can impede usefulness of the product. In these cases, having very distinct bi-modal distributions of particles where the larger particles are not injectable, it is appropriate to ignore those very large particles when calculating the particle size distributions. For example, a composition having about 90% of particles in the range of about 0.02 to about 0.5 microns will be injectable into wood, if the remaining ~10% has, for example, a particle diameter of at least about 5 microns, which size is so large that pore blocking may be reduced or the particle would even settle harmlessly to the bottom of the tank.

The particulate organic biocides of this invention can be incorporated into wood composites, by either being mixed with binder, by coating wood fibers prior to binding, by being injected into wood chips prior to binding, or any combination of the above. Again, a plurality of adjuvants, including sparingly soluble biocidal salts, UV resistant iron oxide pigments, and the like can be milled and added to the wood chips prior to forming the composite. Preferred wood composites have the ground biocide according to this invention (and/or a composition containing same) either mixed with the wood particles before bonding, or preferably injected into the wood particulates and dried prior to bonding.

By "injectable," we mean the ground biocide particulates are able to be pressure-injected into wood, wood products, and the like, to depths normally required in the industry, using equipment, pressures, exposure times, and procedures that are the same or that are substantially similar to those currently used in industry. Pressure treatment is a process performed in a closed cylinder that is pressurized, forcing the chemicals into the wood. In preferred embodiments of the invention, incising is not expected to be required to inject the slurries of the present invention into lumber having thicknesses of about 6 to about 10 inches. Wood or wood products comprising ground biocide particles according to the invention may be prepared by subjecting the wood to vacuum and/or pressure in the presence of a flowable material comprising the ground biocide particles. A pre-injection of carbon dioxide followed by vacuum and then injection of a biocidal slurry is one preferred method of injecting the slurry into wood. Injection of particles into the wood or wood product from a flowable material comprising the particles may require longer pressure treatments than would be required for liquids free of such particles. Pressures of, for example, at least about 75 psi, at least about 100 psi, or at least about 150 psi may be used. Exemplary flowable materials include liquids comprising ground biocide particles, emulsions comprising ground biocide particles, and slurries comprising ground biocide particles. In one embodiment, a volume number density of the ground biocide particles according to the invention about 5 cm from the surface, and preferably throughout the interior of the wood or wood product, is at least about 50%, for example, at least about 60%, at least about 70%, or at least about 75% of the volume number density of the ground biocide particles about 1 cm from the surface.

Advantageously, the particles are not too elongated, or rod-shaped, with a single long dimension. Average particle diameter is beneficially determined by Stokes Law settling velocities of particles in a fluid to a size down to about 0.2 microns. Smaller sizes are beneficially determined by for example a dynamic light scattering method or laser scattering method or electron microscopy. Generally, such a particle size and particle size distribution can be achieved by mechanical attrition of particles.

Attrition can be obtained by wet milling in a sand grinder charged with, for example, partially stabilized zirconia beads with a diameter of about 0.5 mm; alternatively wet milling in a rotary sand grinder with partially stabilized zirconia beads with a diameter of about 0.5 mm and with stirring at, for example, about 1000 rpm or more; or by use of a wet-ball mill, an attritor (e.g., manufactured by Mitsui Mining Ltd.), a pearl mill (e.g., manufactured by Ashizawa Ltd.), or the like. Attrition can be achieved to a lesser degree by centrifugation, but larger particles can be simply removed from the composition via centrifugation. Removing the larger particulates from a composition can provide an injectable formulation. Said particulates can be removed by centrifugation, where settling velocity substantially follows Stokes law.

The most effective method of modifying the particle size distribution is wet milling. Beneficially all injectable formulations for wood treatment should be wet-milled, even when the "mean particle size" is well within the range considered to be "injectable" into wood. Even when a few weight percent of particles exhibit a size above about 1 micron, this small amount of material is hypothesized to form the start of a plug (where smaller, normally injectable particles are subsequently caught by the plug). Further, it is believed that wet milling with larger-sized media (e.g., 2 mm zirconium silicate) will have virtually no effect, resulting in only a marginal decrease in particle size, such that the material will still not be injectable in commercial quantities.

However, it has been found that a milling process using about 0.5 mm high density zirconium-containing (e.g., preferably zirconium oxide) grinding media provides efficient attrition, especially for the removal of particles greater than about 1 micron in the commercially available biocide particulate product. The milling process usually takes on the order of minutes to achieve almost complete removal of particles greater than about 1 micron in size. As stated above, the size of the milling material is believed to be important, even critical, to obtaining a commercially acceptable process. The milling agent material having a diameter of about 1 or 2 mm (or greater) are ineffective, while milling agent material having a diameter of about 0.5 mm and a density of greater than 5.5 grams/cc is effective typically after about 15 to 120 minutes of milling.

EXAMPLES

The following examples are merely indicative of the nature of the present invention, and should not be construed as limiting the scope of the invention, nor of the appended claims, in any manner.

Example 1

Milling Chlorothalonil with 0.5 mm Zirconium Silicate

The laboratory-sized vertical mill was provided by CB Mills, model# L-3-J. The mill has a 2 liter capacity and is jacketed for cooling. Unless otherwise specified, ambient water was cycled through the mill cooling jacket during operation. The internal dimensions are 3.9" diameter by 9.1"

height. The mill uses a standard 3×3" disk agitator (mild steel) on a stainless steel shaft, and it operates at 2,620 rpm.

The media used in this Example was 0.4–0.5 mm zirconium silicate beads supplied by CB Mills. All particle size determinations were made with a Sedigraph™ 5100T manufactured by Micromeritics, which uses x-ray detection and bases calculations of size on Stokes' Law.

The formulation contained 20.41% chlorothalonil (98% active), 5% Galoryl™ DT-120, 2% Morwet™ EFW, and 72.6% water by weight, and the concentrate had a pH of 8.0. The total batch weight was about 600 g. The results of a 7.5 hour grinding study are given in Table 1 below.

TABLE 1

| Milling Time | $d_{50}$ | Particle Size Data - Volume % With Diameter Greater Than | | | |
| --- | --- | --- | --- | --- | --- |
| Mins. | μm | 10 μm | 5 μm | 2 μm | 1 μm |
| 0 | 4.9 | 10 | 48 | 95 | |
| 30 | 1.3 | 0 | 4 | 21 | 68 |
| 60 | 1.0 | 4 | 2 | 11 | 50 |
| 90 | 1.4 | 18 | 23 | 22 | 94 |
| 120 | 1.03 | 2 | 0 | 4 | |
| 150 | 1.12 | 0 | 2 | 6 | 58 |
| 180 | 1.07 | 2 | 2 | 7 | 53 |
| 270 | 1.09 | 2 | 0 | 8 | 54 |
| 450 | 1.15 | 12 | 8 | 21 | 56 |

The results show that chlorothalonil can be wet milled from a starting particle size of about 3–4 microns to a $d_{50}$ near 1 micron within about one hour, using a spherical ~3.8 g/cm³ zirconium silicate media having an average particle size of about 0.4–0.5 mm. Further grinding had little effect, possibly slightly reducing the weight of particles over about 2 microns and thereby reducing the $d_{90}$ from about 2 microns at 60 minutes to slightly less than 2.

However, these results also showed the limitations of this lower density material. In the next example, higher density doped zirconia, having a density of 5.5 to 6.5 g/cc, was used and provided much more effective milling.

Example 2

Milling Chlorothalonil with 0.5 mm Zirconium Oxide

The same mill and conditions were used in this experiment as in experiment 1. However, the grinding media was 0.5–0.6 mm cerium-doped zirconium oxide beads obtained from CB Mills. The density of the cerium doped zirconium oxide is ~6.0 g/cm³. The formulation contained 20.41% chlorothalonil (98% Active), 5% Galoryl™ DT-120, 2% Morwet™ EFW, 3% Pluronic™ F-108, and 69.6% water by weight, and the concentrate had a pH of about 7.3. The total batch weight was about 600 g. The results are shown in Table 2 below.

TABLE 2

| Milling Time | $d_{50}$ | Particle Size Data - Volume % With Diameter Greater Than | | | | | |
| --- | --- | --- | --- | --- | --- | --- | --- |
| Mins. | μm | 10 μm | 5 μm | 2 μm | 1 μm | 0.4 μm | 0.2 μm |
| 0 | 3.44 | 8 | 30 | 77 | 92 | — | — |
| 90 | 0.31 | 3 | 3 | 3 | 3 | 22 | — |
| 240 | 0.21 | 0 | 1 | 2 | 3 | 3 | 51 |

For the higher density 0.5 mm zirconia milling media, a composition with a $d_{50}$ less than 1 micron and a $d_{95}$ less than 1 micron was obtainable in 90 minutes, and a composition with a $d_{50}$ less than 0.3 microns and a $d_{95}$ less than 0.4 microns was obtainable in 6 hours. The product obtained after 90 minutes of milling represents an increase in number of particles per unit of mass by a factor of more than about 30 over the standard products, but the product obtained after 90 minutes of milling represents an increase in number of particles per unit of mass by a factor of more than about 1000 over the standard products. The higher surface areas associated with the smaller particles should give rise to a product with enhanced bioactivity due to an increase in reservoir activity (ability to deliver chlorothalonil to the infection court).

Example 3

Milling Sparingly Soluble Copper Salts with 0.5 mm Zirconium Silicate

This comparative example and subsequent example show the effectiveness of the milling media and process on the particle size distribution of inorganic copper salts.

Comparative Example 3A

Figure 3:
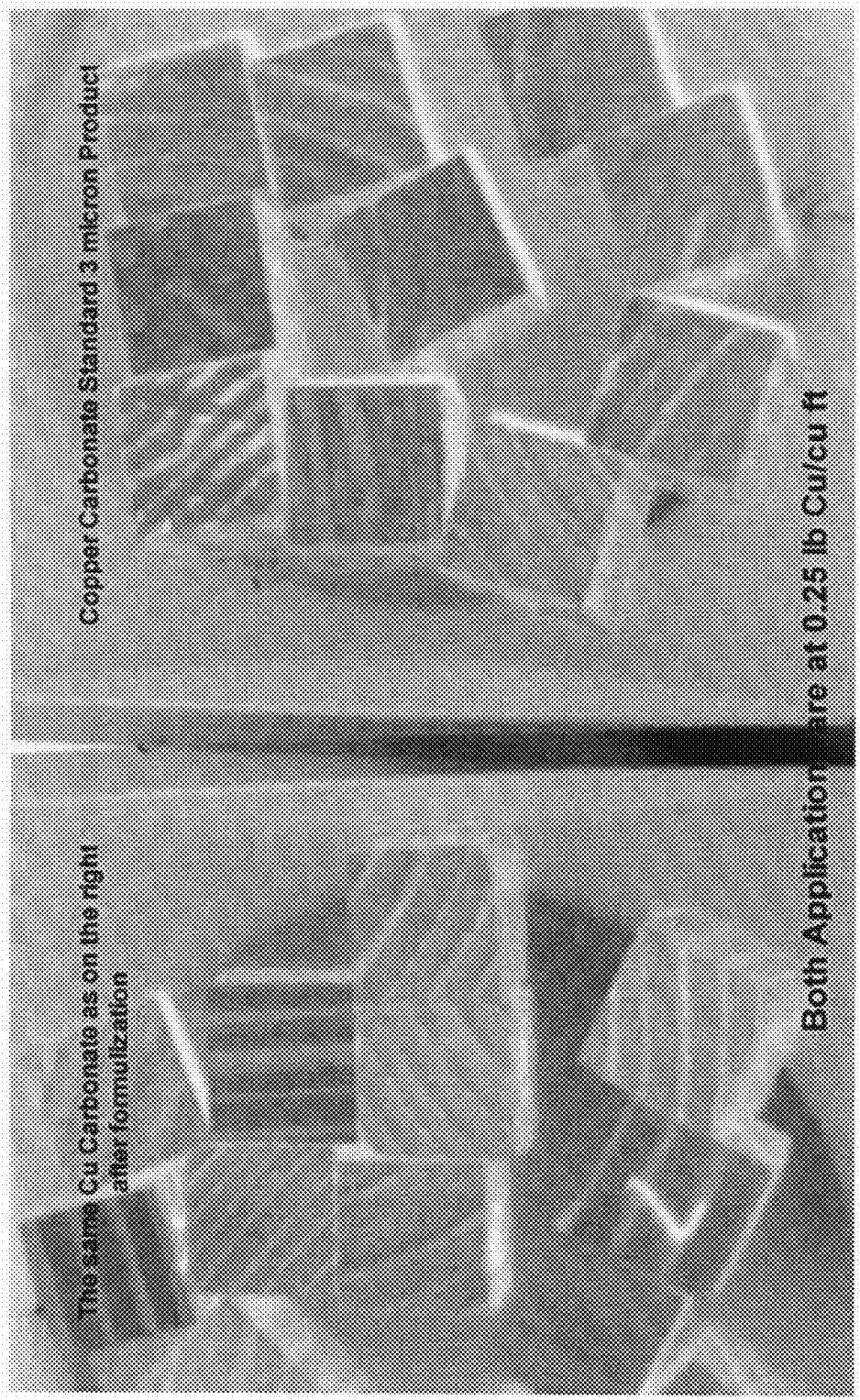

A commercially available a magnesium stabilized form of copper hydroxide particulate material, Champ DP® available from available from Phibro-Tech., Inc., has particles with a $d_{50}$ of about 0.2 microns. FIG. 3 shows the results of trying to inject untreated 2.5 micron $d_{50}$ copper hydroxide into wood. The copper material plugged the surface of the wood and made an unsightly blue-green stain. The results were less dramatic when injecting Champ DP, but were still commercially unacceptable. Analysis of the material found that while the d50 of the material was <0.2 microns, about 13% by weight of the material had diameters between 2 and 5 times greater than the $d_{50}$, and 1% had an even greater diameter.

The Champ DP® material was placed in a mill with about a 50% by volume loading of 2 mm zirconium silicate milling beads. Samples were removed intermittently and the particle size distribution was determined. Wet milling with 2 mm zirconium silicate milling media had no effect—wet milling for days resulted in only a very slight decrease in particle size, a small shift in the particle size distribution, but the material was not injectable into wood In contrast, five samples of particulate copper salts made following standard procedures known in the art were milled according to the method of this invention. The first two samples were copper hydroxide—one with an initial particle size $d_{50}$ of <0.2 microns (the material of comparative example A), and the second with an initial $d_{50}$ of 2.5 microns. A basic copper carbonate (BCC) salt was prepared and it had an initial $d_{50}$ of 3.4 microns. A tribasic copper sulfate salt was prepared and this material has a $d_{50}$ of 6.2 micron. Finally, a copper oxychloride (COc) sample was prepared and this material has an initial $d_{50}$ of 3.3 microns. Selected surface active agents were added to each slurry, and the initial slurries were each in turn loaded into a ball mill having 0.5 mm zirconium silicate (density 3.8 grams/cm3) at about 50% of mill volume, and milled at about 2600 rpm for about a half hour. The particle size distribution of the milled material was then determined. The particle size distribution data is shown in Table 1. It can be seen that even with the relatively modest zirconium silicate milling media, injectable compositions were obtained in about 30 minutes milling time or less.

TABLE 1

Particle Size Distribution Before/After Milling (0.5 mm Zirconium Silicate)

| Material | d50 | % < 10μ | % < 1μ | % < 0.4μ | % < 0.2μ |
|---|---|---|---|---|---|
| Cu(OH)$_2$, before milling | <0.2 | 99% | 84% | 64% | 57% |
| Cu(OH)$_2$, after milling | <0.2 | 99% | 97% | 95% | 85% |
| Cu(OH)2, before milling | 2.5 | 99% | 9% | — | — |
| Cu(OH)2, after milling | 0.3 | 99.7% | 95% | 22% | —% |
| BCC*, before milling | 3.4 | 98% | 1.2% | — | — |
| BCC*, after milling | <0.2 | 99% | 97% | 97% | 87% |
| TBS*, before milling | 6.2 | 70% | 17% | — | — |
| TBS*, after milling | <0.2 | 99.5% | 96% | 91% | 55% |
| COc*, before milling | 3.3 | 98.5% | 3% | — | — |
| COc*, after milling | 0.38 | 99.4% | 94% | 63% | — |

It can be seen that even the less effective milling media, ~0.5 mm zirconium silicate, was useful for milling sparingly soluble copper salts to the sub-micron particle size distribution needed for treating wood, for incorporating into non-fouling paints and coatings, and for foliar treatments. Further, the rate of particle size attrition is so great that there is no need to use expensive precipitation techniques to provide a feedstock having a sub-micron $d_{50}$. The initial d50 ranged from 0.2 microns to over 6 microns, but after 30 minutes or less of milling each of the above milled copper salts (milling about 15 to about 30 minutes) were injected into wood samples with no discernible plugging.

Milling with the more preferred zirconium oxide milling beads will provide a smaller d50 and will further reduce the amount of material, if any, having a diameter greater than 1 micron. Particulate biocides have an advantage over dispersed or soluble biocides in that the material leaches more slowly from wood than would comparable amounts of soluble biocides, and also about the same or more slowly than comparable amounts of the same biocide applied to the same wood as an emulsion.

Example 4

Injecting Milled Copper Salt Slurries into Wood

Slurries of the above milled sparingly soluble copper salts were successfully injected into standard 1" cubes of Southern Yellow Pine wood. The injection procedures emulated standard conditions used in the industry.

FIG. 3 shows representative photographs showing the comparison of the unacceptable product, which had a $d_{50}$ of 2.5 microns yet still plugged the wood, is shown in comparison with blocks injected with the product milled according to the process of this invention as described in Example 3. FIG. 3 shows the clean appearance of the wood blocks injected with the milled copper hydroxide, to compare with the photograph of the wood samples injected with the un-milled ($d_{50}$<0.2 micron) copper hydroxide. Unlike the blocks injected with un-milled material, wood blocks injected with milled material showed little or no color or evidence of injection of copper-containing particulate salts.

Copper development by colorimetric agents (dithio-oxamide/ammonia) showed the copper to be fully penetrated across the block in the sapwood portion. FIG. 1 shows the penetration of injected particulate copper hydroxide developed with dithio-oxamide in the third picture. The stain corresponds to copper. It can be seen in FIG. 1 that the copper is evenly dispersed throughout the wood. Subsequent acid leaching and quantitative analysis of the copper from two blocks showed that loadings of about 95% and about 104% of expectation (or essentially 100% average of expectation) had occurred. At 100% loading, values of 0.22 lb/ft$^3$ of copper would be obtained.

Example 5

Leaching Copper from Treated Wood

Copper leaching rates from the wood samples prepared in Example 4 were measured following the AWPA Standard Method E11-97. There are two comparative examples—leaching data was obtained from a wood block preserved with a prior art soluble solution of copper MEA carbonate and from a prior art wood block preserved with CCA. The leach rates of the various wood blocks treated with the preservatives prepared according to this invention were far below the leach rates of wood treated with soluble copper carbonate and were even below leach rates of samples treated with CCA.

Figure 2:
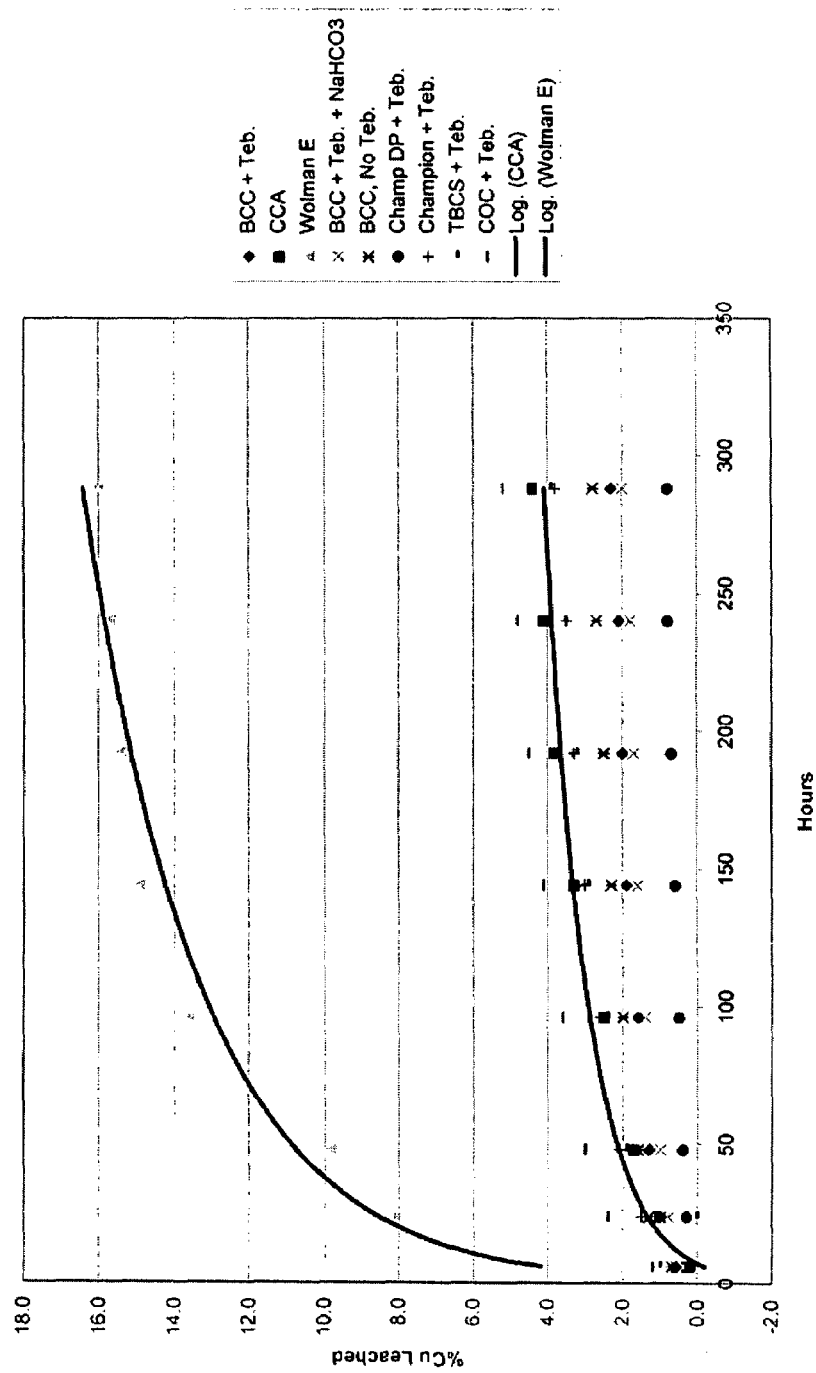

Leaching data from wood was measured following the AWPA Standard Method E11-97 for the following preservative treatments, where, unless specified, the tebuconazole (TEB) concentration was added as an emulsion at 3% of the weight of the added copper: A) TEB and injected basic copper carbonate particulates; B) traditionally CCA-treated wood (as a control); C) TEB and copper methanolamine carbonate (as a control, believed to approximate the currently available Wolman E treatment); D) TEB and injected basic copper carbonate particulates and with sodium bicarbonate buffer; E) Injected basic copper carbonate particulates; F) TEB and injected copper hydroxide particulates modified with zinc and magnesium; G) about 5% TEB and injected copper hydroxide particulates modified with phosphate coating; H) TEB and injected tribasic copper sulfate particulates; and I) TEB and injected copper oxychloride particulates. The leaching data for the various particulate slurries and from two controls are shown in FIG. 2.

The total copper leached from wood preserved with copper-MEA-carbonate was 5.7% at 6 hours, 8.5% at 24 hours, 11% at 48 hours, 22% at 96 hours, 36% at 144 hours, 49% at 192 hours, 62% at 240 hours, 69% at 288 hours, and 76% at 336 hours. The amount of copper leached from copper hydroxide particulates was 0.4% at 6 hours, 0.6% at 24 hours, 0.62% at 48 hours, 1.0% at 96 hours, 1.6% at 144 hours, 2.1% at 192 hours, 3.2% at 240 hours, 3.4% at 288 hours, and 3.7% at 336 hours. The difference in leach rate was greater than a factor of 20.

The leaching data is generally consistent within the small amount of copper leached from these wood samples. Using the copper leach rate of CCA as a standard, and viewing the total leached copper at 96 and 240 hours as representative, the leach rate ratios given by the "total leached copper to total CCA-leached copper" is given in Table 3 below.

Of the sparingly soluble salts used, the leach rate, in descending order, is as follows: copper MEA carbonate (comparative)>>copper oxychloride>tribasic copper sulfate and/or copper hydroxide with phosphate>basic copper carbonate>copper hydroxide with Zn and Mg. The isoelectric point of copper oxychloride is about 5 to about 5.5, and the isoelectric point of tribasic copper sulfate is about 6 to about 6.5. As these materials are very poor bases, the higher leach rates from the materials is consistent with expected higher solubility at lower pH values. The presence of TEB reduced leach rates from basic copper carbonate by about 20%, most likely due to TEB partially coating particulates. A buffering system, sodium bicarbonate, reduced the leach rates from TEB/basic copper carbonate by about 10% relative to a preservative without the buffer.

TABLE 3

| Ex. | Description of Preservative System | 96 hr. ratio to CCA | 240 hr. ratio to CCA |
|---|---|---|---|
| A | 3% TEB and basic copper carbonate particulates | 0.67:1 | 0.51:1 |
| C | 3% TEB and copper MEA carbonate (comparative) | 5.2:1 | 3.85:1 |
| D | 3% TEB and basic copper carbonate particulates with sodium bicarbonate buffer | 0.54:1 | 0.46:1 |
| E | basic copper carbonate particulates | 0.77:1 | 0.63:1 |
| F | 3% TEB and copper hydroxide with Zn and Mg particulates | 0.2:1 | 0.19:1 |
| G | 5% TEB and copper hydroxide particulates modified with phosphate coating | 1.0:1 | 0.88:1 |
| H | 3% TEB and tribasic copper sulfate particulates | 0.96:1 | 0.88:1 |
| I | 3% TEB and copper oxychloride particulates | 1.4:1 | 1.17:1 |

Use of the small diameter milling material, preferably 0.3 mm to 0.6 mm, is essential to make a product that can be confidently sold for injection into wood.

Example 5

Toxicity Evaluation

A sample of treated wood was sent to an outside source for short-duration toxicity testing. The results suggest there is no difference in the Threshold Toxicity between wood treated with a copper MEA carbonate/tebuconazole formulation and wood treated with a identical loading of basic copper carbonate particles of this invention admixed (and partially coated with) the same quantity of tebuconazole.

The invention is meant to be illustrated by these examples, but not limited to these examples.

What is claimed is:

1. A milled chlorothalonil product comprising:
chlorothalonil particles, wherein the chlorothalonil particles have a mean volume particle diameter $d_{50}$ of about 0.6 microns or less and a $d_{90}$, which is a diameter such that 90 volume percent of the particles have a diameter of the $d_{90}$, or less, of less than 1 micron.

2. The chlorothalonil product of claim 1 wherein the $d_{50}$ is about 0.4 microns or less.

3. The chlorothalonil product of claim 1 wherein the $d_{50}$ is about 0.4 microns or less and the $d_{90}$ is less than 0.7 microns.

4. The chlorothalonil product of claim 1 wherein the $d_{50}$ is between about 0.1 and about 0.3 microns.

5. The chlorothalonil product of claim 1 wherein the chlorothalonil particles have a mean volume particle diameter $d_{98}$, which is a diameter such that 98 volume percent of the product has a diameter of the $d_{98}$ or less, of about 0.5 microns or less.

6. The chlorothalonil product of claim 5 wherein product is dispersed in wood.

7. The chlorothalonil product of claim 5 wherein the $d_{98}$ is less than about 0.3 microns.

8. The chlorothalonil product of claim 1 wherein the chlorothalonil particles have a mean volume particle diameter $d_{99}$, such that 99 volume percent of the product has a diameter of the $d_{99}$ or less of less than about 0.7 microns.

9. The chlorothalonil product of claim 8 wherein the product is dispersed in wood.

10. The chlorothalonil product of claim 1 wherein the chlorothalonil particles have a mean volume particle diameter $d_{96}$, such that 96 volume percent of the particles have a diameter of the $d_{96}$ or less of less than about 0.6 microns.

11. The chlorothalonil product of claim 1 wherein the $d_{50}$ is between about 0.1 and about 0.3 microns and where 80% by weight of the chlorothalonil particles have a size/diameter between about 0.05 microns and about 0.4 microns.

12. The chlorothalonil product of claim 6 wherein the $d_{98}$ is less than about 0.2 microns.

13. The chlorothalonil product of claim 1 wherein the $d_{50}$ is between about 0.1 and about 0.3 microns and the $d_{90}$ is less than about 0.4 microns.

14. The chlorothalonil product of claim 13 wherein the product is dispersed in wood.

15. A milled chlorothalonil product comprising:
chlorothalonil particles,
wherein the chlorothalonil particles have a mean volume particle diameter $d_{50}$ of about 0.7 microns or less and a $d_{90}$ which is a diameter such that 90 volume percent of the particles have a diameter of the $d_{90}$ or less, of less than 3 times the $d_{50}$.

16. The chlorothalonil product of claim 15 wherein the particles have a $d_{10}$, which is a diameter such that 10 volume percent of the particles have a diameter of the $d_{10}$ or less, of greater than 0.25 times the $d_{50}$.

17. The chlorothalonil product of claim 15 wherein the $d_{50}$ is less than about 0.4 microns.

18. The chlorothalonil product of claim 15 wherein the $d_{50}$ is between about 0.1 and about 0.3 microns.

19. The chlorothalonil product of claim 15 wherein the chlorothalonil particles are is contained in an aqueous slurry further comprising dispersants and stabilizers.

20. The chlorothalonil product of claim 15 wherein the chlorothalonil particles are contained in an aqueous slurry further comprising between about 2% and about 60% by weight of dispersants and stabilizers, based on the weight of the chlorothalonil.

21. The chlorothalonil product of claim 15 wherein the product further comprises surface active agents in an amount such that the chlorothalonil particles are non-agglomerating and non-interacting in an aqueous dispersion.

22. The chlorothalonil product of claim 15 wherein the $d_{90}$ is less than two times the $d_{50}$.

23. The chlorothalonil product of claim 22 wherein the $d_{50}$ is about 0.2 microns.

24. The chlorothalonil product of claim 23 wherein the particles have a mean volume particle diameter $d_{10}$, such that about 10 volume percent of the particles have a diameter of the $d_{10}$ or less, of greater than 0.25 times the $d_{50}$.

25. The chlorothalonil product of claim 22 wherein the product is dispersed on foliage.

26. The chlorothalonil product of claim 22 wherein the product is dispersed in non-fouling paint.

* * * * *